US007776834B2

(12) United States Patent
Agrawal et al.

(10) Patent No.: US 7,776,834 B2
(45) Date of Patent: Aug. 17, 2010

(54) IMMUNOSTIMULATORY PROPERTIES OF OLIGONUCLEOTIDE-BASED COMPOUNDS COMPRISING MODIFIED IMMUNOSTIMULATORY DINUCLEOTIDES

(75) Inventors: Sudhir Agrawal, Shrewsbury, MA (US); Dong Yu, Westboro, MA (US); Ekambar Kandimalla, Southboro, MA (US)

(73) Assignee: Idera Pharmaceuticals, Inc., Cambridge, MA (US)

( * ) Notice: Subject to any disclaimer, the term of this patent is extended or adjusted under 35 U.S.C. 154(b) by 1317 days.

(21) Appl. No.: 11/268,714

(22) Filed: Nov. 7, 2005

(65) Prior Publication Data
US 2007/0105801 A1 May 10, 2007

(51) Int. Cl.
A61K 31/70 (2006.01)
A61K 38/00 (2006.01)
A61K 37/18 (2006.01)
A61K 39/00 (2006.01)
A61K 39/35 (2006.01)
A61K 39/36 (2006.01)
A01N 43/04 (2006.01)
C07H 21/02 (2006.01)
C07H 21/04 (2006.01)

(52) U.S. Cl. ............ 514/44; 514/2; 424/184.1; 424/278.1; 424/275.1; 536/23.1; 530/387.1

(58) Field of Classification Search ............ None
See application file for complete search history.

(56) References Cited

U.S. PATENT DOCUMENTS

| 5,149,798 | A  | 9/1992  | Agrawal et al.  |
| 5,366,878 | A  | 11/1994 | Pederson et al. |
| 5,635,377 | A  | 6/1997  | Pederson et al. |
| 5,652,355 | A  | 7/1997  | Metelev et al.  |
| 5,912,332 | A  | 6/1999  | Agrawal et al.  |
| 6,143,881 | A  | 11/2000 | Metelev et al.  |
| 6,346,614 | B1 | 2/2002  | Metelev et al.  |
| 6,426,334 | B1 | 7/2002  | Agrawal         |
| 6,476,000 | B1 | 11/2002 | Agrawal         |
| 6,815,429 | B2 | 11/2004 | Agrawal         |
| 7,115,579 | B2 | 10/2006 | Agrawal         |
| 7,262,286 | B2 | 8/2007  | Kandimalla      |

FOREIGN PATENT DOCUMENTS

WO WO 2004/064782 A2 * 8/2004

OTHER PUBLICATIONS

Paul S. Cur Opin Mol Ther Oct. 2003; 5(5):553-9.*
Zon, Gerald, "Oligonucleoside Phosphorothioates", Protocols for Oligonucleotides and Analogs, 20:165-189 (1993).
Zon et al., "Phosphorothioate Oligonucleotides", pp. 87-108 (1991).
Agrawal et al., "Modified Oligonucleotides as Therapeutic and Diagnostic Agents" Curr. Op. in Biotech. 6:12-19 (1995).
Khorana et al., "Studies on Polynucleotides", J. Molec. Biol. 72:209-217 (1972).
Reese, Colin B., "The Chemical Synthesis of Oligo- and Poly-Nucleotides by the Phosphotriester Approach", Tetrahedron Lett. 34:3143-3179 (1978).
Beaucage et al., "Deoxynucleoside Phosphoramidites-A New Class of Key Intermediates for Deoxypolynucleotide Synthesis", Tetrahedron Lett. 22:1859-1862 (1981).
Agrawal et al., "Oligodeoxynucleoside Methylphosphonates: Synthesis and Enzymic Degradation", Tetrahedron Lett. 28:3539-3542 (1987).
Connolly et al., "Synthesis and Characterization of an Octanucleotide Containing the *Eco*RI Recognition Sequence with a Phosphorotioate Group at the Cleavage Site", Biochem. 23:3443-3453 (1984).
Jager et al., "Oligonucleotide N-Alkylphosphoroamidates: Synthesis and Binding to Polynucleotides", Biochem. 27:7237-7246 (1988).
Agrawal et al., "Oligodeoxynucleoside Phosphoramidites and Phosphorothioates as Inhibitors of Human Immunodeficiency Virus", Proc. Natl. Acad. Sci. (USA) 85:7079-7083 (1988).
Kuramoto et al., "Oligonucleotides Sequences Required for natural Killer Cell Activation", Jpn. J. Cancer Res. 83:1128-1131 (1992).
Krieg et al., "CpG Motifs in Bacterial DNA Trigger Direct B-Cell Activation", Nature 371:546-549 (1995).
Liang et al., "Activation of Human B Cells by Phosphorothioate Oligodeoxynucleotides", J. Clin. Invest. 92:1119-1129 (1996).
Moldoveanu et al., "CpG DNA, A Novel Immune Enhancer . . . " Vaccine 16:1216-1224 (1998).
McCluskie et al., "Cutting Edge: CpG DNA is a Potent . . . " J. Immunol. 161:4463-4466 (1998).
Hartman et al., "Delineation of a CpG Phosphorothioate . . . " J. Immunol. 164:1617-1624 (2000).
Zhao et al., "Effect of Different Chemically Modified Oligodeoxynucleotides on Immune Stimulation", Biochem. Pharm. 51:173-182 (1996).
Zhao et al., "Modulation of Oligonucleotide-Induced Immune Stimulation by Cyclodextrin Analogs", Biochem. Pharm. 52:1537-1544 (1996).
Zhao et al., "pattern and Kinetics of Cytokine production Following Administration of Phosphorotioate Oligonucleotides in Mice", Antisense Nucleic Acid Drug Devel. 7:495-502 (1997).

(Continued)

*Primary Examiner*—Robert Mondesi
*Assistant Examiner*—Oluwatosin Ogunbiyi
(74) *Attorney, Agent, or Firm*—Wayne A. Keown; Preti Flaherty

(57) ABSTRACT

The invention relates to the therapeutic use of oligonucleotides as immunostimulatory agents in immunotherapy applications. More particularly, the invention provides an immunostimulatory oligonucleotides for use in methods for generating an immune response or for treating a patient in need of immunostimulation. The immunostimulatory oligonucleotides of the invention preferably comprise novel purines. The immunostimulatory oligonucleotides according to the invention further comprise at least two oligonucleotides linked at their 3' ends, internucleoside linkages or functionalized nucleobase or sugar to a non-nucleotidic linker, at least one of the oligonucleotides being an immunostimulatory oligonucleotide and having an accessible 5' end.

31 Claims, 10 Drawing Sheets

OTHER PUBLICATIONS

Zhao et al., "Site of Chemical Modifications in CpG Containing Phosphorothioate Oligodeoxynucleotide Modulates Its Immunostimulatory Activity", Bioorg. Med. Chem. Lett. 9:3453-3458 (1999).

Zhao et al., "Immunostimulatory Activity of CpG Containing . . . ", Bioorg. Med. Chem. Lett. 10:1051-1054 (2000).

Yu et al., "Modulation of Immunostimulatory Activity of CpG Oligonucleotides by Site-specific Deletion of Nucleobases", Bioorg. Med. Chem. Lett. 11:2263-2267 (2001).

Kandimalla et al., "Effect of Chemical Modifications of Cytosine and Guanine in a CpG Motif of Oligonucleotides: Structure-Immunostimulatory Activity Relationships", Bioorg. Med. Chem. 9:807-813 (2001).

* cited by examiner

SEQUENCE LISTING

```
<160> NUMBER OF SEQ ID NOS: 17

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 1-(2'-deoxy-beta-D-ribofuranosyl)-2-oxo-7-
      deaza-8-methyl-purine

<400> SEQUENCE: 1
tctgtngttc t                                                          11

<210> SEQ ID NO 2
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
acacaccaac t                                                          11

<210> SEQ ID NO 3
<211> LENGTH: 11
```

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 1-(2'-deoxy-beta-D-ribofuranosyl)-2-oxo-7-
      deaza-8-methyl-purine
<220> FEATURE:
<221> NAME/KEY: modified_base
<222> LOCATION: (10)..(11)
<223> OTHER INFORMATION: 2'-O-methyl-ribonucleotide

<400> SEQUENCE: 3
tctgtngttc u                                                          11

<210> SEQ ID NO 4
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: 1-(2'-deoxy-beta-D-ribofuranosyl)-2-oxo-7-
      deaza-8-methyl-purine

<400> SEQUENCE: 4
ctgtngttct c                                                          11

<210> SEQ ID NO 5
<211> LENGTH: 11
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: 1-(2'-deoxy-beta-D-ribofuranosyl)-2-oxo-7-
      deaza-8-methyl-purine
<220> FEATURE:
<221> NAME/KEY: modified_base
<222> LOCATION: (10)..(11)
<223> OTHER INFORMATION: 2'-O-methyl-ribonucleotide

<400> SEQUENCE: 5
ctgtngttcu c                                                          11

<210> SEQ ID NO 6
<211> LENGTH: 11
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
```

<223> OTHER INFORMATION: 1-(2'-deoxy-beta-D-ribofuranosyl)-2-oxo-7-
      deaza-8-methyl-purine
<220> FEATURE:
<221> NAME/KEY: modified_base
<222> LOCATION: (9)..(11)
<223> OTHER INFORMATION: 2'-O-methyl-ribonucleotide

<400> SEQUENCE: 6
ctgtngttcu c                                                              11

<210> SEQ ID NO 7
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 1-(2'-deoxy-beta-D-ribofuranosyl)-2-oxo-7-
      deaza-8-methyl-purine

<400> SEQUENCE: 7
tctgtngttc t                                                              11

<210> SEQ ID NO 8
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 1-(2'-deoxy-beta-D-ribofuranosyl)-2-oxo-7-
      deaza-8-methyl-purine

<400> SEQUENCE: 8
tctgtngaca g                                                              11

<210> SEQ ID NO 9
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 1-(2'-deoxy-beta-D-ribofuranosyl)-2-oxo-7-
      deaza-8-methyl-purine
<220> FEATURE:
<221> NAME/KEY: modified_base
<222> LOCATION: (10)..(11)
<223> OTHER INFORMATION: 2'-O-methyl-ribonucleotide

<400> SEQUENCE: 9
tctgtngaca g                                                              11

<210> SEQ ID NO 10
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base

```
<222> LOCATION: (6)
<223> OTHER INFORMATION: 1-(2'-deoxy-beta-D-ribofuranosyl)-2-oxo-7-
      deaza-8-methyl-purine

<400> SEQUENCE: 10
tcagtngtta g                                                          11

<210> SEQ ID NO 11
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 1-(2'-deoxy-beta-D-ribofuranosyl)-2-oxo-7-
      deaza-8-methyl-purine

<400> SEQUENCE: 11
tcagtngact g                                                          11

<210> SEQ ID NO 12
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)
<223> OTHER INFORMATION: 1-(2'-deoxy-beta-D-ribofuranosyl)-2-oxo-7-
      deaza-8-methyl-purine
<220> FEATURE:
<221> NAME/KEY: modified_base
<222> LOCATION: (5)
<223> OTHER INFORMATION: 1-(2'-deoxy-beta-D-ribofuranosyl)-2-oxo-7-
      deaza-8-methyl-purine
<220> FEATURE:
<221> NAME/KEY: modified_base
<222> LOCATION: (8)
<223> OTHER INFORMATION: 1-(2'-deoxy-beta-D-ribofuranosyl)-2-oxo-7-
      deaza-8-methyl-purine

<400> SEQUENCE: 12
tngtnganga t                                                          11

<210> SEQ ID NO 13
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)
<223> OTHER INFORMATION: 1-(2'-deoxy-beta-D-ribofuranosyl)-2-oxo-7-
      deaza-8-methyl-purine
<220> FEATURE:
<221> NAME/KEY: modified_base
<222> LOCATION: (5)
<223> OTHER INFORMATION: 1-(2'-deoxy-beta-D-ribofuranosyl)-2-oxo-7-
      deaza-8-methyl-purine

<400> SEQUENCE: 13
tngtngtagt a                                                          11

<210> SEQ ID NO 14
```

```
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)
<223> OTHER INFORMATION: 1-(2'-deoxy-beta-D-ribofuranosyl)-2-oxo-7-
      deaza-8-methyl-purine
<220> FEATURE:
<221> NAME/KEY: modified_base
<222> LOCATION: (6)
<223> OTHER INFORMATION: 1-(2'-deoxy-beta-D-ribofuranosyl)-2-oxo-7-
      deaza-8-methyl-purine

<400> SEQUENCE: 14
tngaangttc t                                                          11

<210> SEQ ID NO 15
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)
<223> OTHER INFORMATION: 1-(2'-deoxy-beta-D-ribofuranosyl)-2-oxo-7-
      deaza-8-methyl-purine
<220> FEATURE:
<221> NAME/KEY: modified_base
<222> LOCATION: (6)
<223> OTHER INFORMATION: 1-(2'-deoxy-beta-D-ribofuranosyl)-2-oxo-7-
      deaza-8-methyl-purine

<400> SEQUENCE: 15
tngtangtac t                                                          11

<210> SEQ ID NO 16
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (7)
<223> OTHER INFORMATION: 2'-deoxy-7-deazaguanosine
<220> FEATURE:
<221> NAME/KEY: modified_base
<222> LOCATION: (11)
<223> OTHER INFORMATION: 2'-deoxy-7-deazaguanosine

<400> SEQUENCE: 16
tcnaacnttc n                                                          11

<210> SEQ ID NO 17
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 17
tgcaagcttg c                                                              11
```

IMMUNOSTIMULATORY PROPERTIES OF OLIGONUCLEOTIDE-BASED COMPOUNDS COMPRISING MODIFIED IMMUNOSTIMULATORY DINUCLEOTIDES

BACKGROUND OF THE INVENTION

1. Field of the Invention

The invention relates to immunology and immunotherapy applications using oligonucleotides as immunostimulatory agents.

2. Summary of the Related Art

Oligonucleotides have become indispensable tools in modern molecular biology, being used in a wide variety of techniques, ranging from diagnostic probing methods to PCR to antisense inhibition of gene expression and immunotherapy applications. This widespread use of oligonucleotides has led to an increasing demand for rapid, inexpensive and efficient methods for synthesizing oligonucleotides.

The synthesis of oligonucleotides for antisense and diagnostic applications can now be routinely accomplished. See, e.g., *Methods in Molecular Biology*, Vol. 20: *Protocols for Oligonucleotides and Analogs* pp. 165-189 (S. Agrawal, ed., Humana Press, 1993); *Oligonucleotides and Analogues, A Practical Approach*, pp. 87-108 (F. Eckstein, ed., 1991); and Uhlmann and Peyman, supra; Agrawal and Iyer, *Curr. Op. in Biotech.* 6:12 (1995); and *Antisense Research and Applications* (Crooke and Lebleu, eds., CRC Press, Boca Raton, 1993). Early synthetic approaches included phosphodiester and phosphotriester chemistries. For example, Khorana et al., *J. Molec. Biol.* 72:209 (1972) discloses phosphodiester chemistry for oligonucleotide synthesis. Reese, *Tetrahedron Lett.* 34:3143-3179 (1978), discloses phosphotriester chemistry for synthesis of oligonucleotides and polynucleotides. These early approaches have largely given way to the more efficient phosphoramidite and H-phosphonate approaches to synthesis. For example, Beaucage and Caruthers, *Tetrahedron Lett.* 22:1859-1862 (1981), discloses the use of deoxyribonucleoside phosphoramidites in polynucleotide synthesis. Agrawal and Zamecnik, U.S. Pat. No. 5,149,798 (1992), discloses optimized synthesis of oligonucleotides by the H-phosphonate approach. Both of these modern approaches have been used to synthesize oligonucleotides having a variety of modified internucleotide linkages. Agrawal and Goodchild, *Tetrahedron Lett.* 28:3539-3542 (1987), teaches synthesis of oligonucleotide methylphosphonates using phosphoramidite chemistry. Connolly et al., *Biochem.* 23:3443 (1984), discloses synthesis of oligonucleotide phosphorothioates using phosphoramidite chemistry. Jager et al., *Biochem.* 27:7237 (1988), discloses synthesis of oligonucleotide phosphoramidates using phosphoramidite chemistry. Agrawal et al., *Proc. Natl. Acad Sci. (USA)* 85:7079-7083 (1988), discloses synthesis of oligonucleotide phosphoramidates and phosphorothioates using H-phosphonate chemistry.

More recently, several researchers have demonstrated the validity of the use of oligonucleotides as immunostimulatory agents in immunotherapy applications. The observation that phosphodiester and phosphorothioate oligonucleotides can induce immune stimulation has created interest in developing this side effect as a therapeutic tool. These efforts have focused on phosphorothioate oligonucleotides containing the dinucleotide natural CpG. Kuramoto et al., *Jpn. J. Cancer Res.* 83:1128-1131 (1992) teaches that phosphodiester oligonucleotides containing a palindrome that includes a CpG dinucleotide can induce interferon-alpha and gamma synthesis and enhance natural killer activity. Krieg et al., *Nature* 371:546-549 (1995) discloses that phosphorothioate CpG-containing oligonucleotides are immunostimulatory. Liang et al., *J. Clin. Invest.* 98:1119-1129 (1996) discloses that such oligonucleotides activate human B cells. Moldoveanu et al., *Vaccine* 16:1216-124 (1998) teaches that CpG-containing phosphorothioate oligonucleotides enhance immune response against influenza virus. McCluskie and Davis, *J. Immunol.* 161:4463-4466 (1998) teaches that CpG-containing oligonucleotides act as potent adjuvants, enhancing immune response against hepatitis B surface antigen. Hartman et al., J. Immunol 164: 1617-1624 (2000) teaches that the immunostimulatory sequence is species specific, and different between mice and primates.

Other modifications of CpG-containing phosphorothioate oligonucleotides can also affect their ability to act as modulators of immune response. See, e.g., Zhao et al., *Biochem. Pharmacol.* (1996) 51:173-182; Zhao et al., *Biochem Pharmacol.* (1996) 52:1537-1544; Zhao et al., *Antisense Nucleic Acid Drug Dev.* (1997) 7:495-502; Zhao et al., *Bioorg. Med. Chem. Lett.* (1999) 9:3453-3458; Zhao et al., *Bioorg. Med. Chem. Lett.* (2000) 10:1051-1054; Yu et al., *Bioorg. Med. Chem. Lett.* (2000) 10:2585-2588; Yu et al., *Bioorg. Med. Chem. Lett.* (2001) 11:2263-2267; and Kandimalla et al., *Bioorg. Med. Chem.* (2001) 9:807-813.

These reports make clear that there remains a need to be able to modulate the immune response caused by immunostimulatory oligonucleotides and to overcome species specificity of the immunostimulatory sequences.

BRIEF SUMMARY OF THE INVENTION

The invention provides methods for modulating the immune response caused by oligonucleotide compounds. The methods according to the invention enable modifying the cytokine profile produced by immunostimulatory oligonucleotides for immunotherapy applications. The present inventors have surprisingly discovered that modification of immunostimulatory dinucleotides allows flexibility in the nature of the immune response produced and that certain modifications overcome the species specificities observed to date of the immunostimulatory sequences.

In a first aspect the invention provides an immunostimulatory oligonucleotide having a structure from the group of 5'-TCTGTR'GTTCT-X-TCTTGR'TGTCT-5' (5'-SEQ ID NO: 1-3'-X-3'-SEQ ID NO: 1-5'); 5'-TCTGTR'GTTC$_1$U$_1$-X-U$_1$C$_1$TTGR'TGTCT-5' (5'-SEQ ID NO: 3-3'-X-3'-SEQ ID NO: 3-5'); 5'-CTGTR'GTTCTC-X-CTCTTGR'TGTC-5' (5'-SEQ ID NO: 4-3'-X-3'-SEQ ID NO: 4-5'); 5'-CTGTR'GTTCU$_1$C$_1$-X-C$_1$U$_1$CTTGR'TGTC-5' (5'-SEQ ID NO: 5-3'-X-3'-SEQ ID NO: 5-5'); 5'-CTGTR'GTTC$_1$U$_1$C$_1$-X-C$_1$U$_1$C$_1$TTGR'TGTC-5' (5'-SEQ ID NO: 6-3'-X-3'-SEQ ID NO: 6-5'); 5'-TCTGTR'GTTCT-X-CGTTCGAACGT-5' (5'-SEQ ID NO: 7-3'-X-3'-SEQ ID NO: 17-5'); 5'-TCTGTR'GACAG-X-GACAGR'TGTCT-5' (5'-SEQ ID NO: 8-3'-X-3'-SEQ ID NO: 8-5'); 5'-TCTGTR'GACA$_1$G$_1$-X-G$_1$A$_1$CAGR'TGTCT-5' (5'-SEQ ID NO: 9-3'-X-3'-SEQ ID NO: 9-5'); 5'-TCAGTR'GTTAG-X-GATTGR'TGACT-5' (5'-SEQ ID NO: 10-3'-X-3'-SEQ ID NO: 10-5'); 5'-TCAGTR'GACTG-X-GTCAGR'TGACT-5' (5'-SEQ ID NO: 11-3'-X-3'-SEQ ID NO: 11-5'); 5'-TR'GTR'GAR'GAT-X-TAGR'AGR'TGR'T-5' (5'-SEQ ID NO: 12-3'-X-3'-SEQ ID NO: 12-5'); 5'-TR'GTR'GTAGTA-X-ATGATGR'TGR'T-5' (5'-SEQ ID NO: 13-3'-X-3'-SEQ ID NO: 13-5'); 5'-TR'GAAR'GTTCT-X-TCTTGR'AAGR'T-5' (5'-SEQ ID NO: 14-3'-X-3'-SEQ ID NO: 14-5'); and 5'-TR'GTAR'GTACT-X-TCATGR'ATGR'T-5' (5'-SEQ ID NO: 15-3'-X-3'-SEQ ID NO: 15-5'); 5'-TCRAACRTTCR-X-RCTTRCAARCT-5' (5'-SEQ(5'-

SEQ ID NO: 16-3'-X-3'-SEQ ID NO: 16-5'), wherein R'=1-(2'-deoxy-β-D-ribofuranosyl)-2-oxo-7-deaza-8-methyl-purine; $A_1/C_1/G_1/U_1$=2'-O-methyl-ribonucleotides; R=2'-deoxy-7-deazaguanosine and X=glycerol linker.

In a third aspect the invention provides a method for generating an immune response in a vertebrate, the method comprising administering to the vertebrate an immunostimulatory oligonucleotide having a structure from the group of 5'-TCTGTR'GTTCT-X-TCTTGR'TGTCT-5' (5'-SEQ ID NO: 1-3'-X-3'-SEQ ID NO: 1-5'); 5'-TCTGTR'GTTC$_1$U$_1$-X-U$_1$C$_1$TTGR'TGTCT-5' (5'-SEQ ID NO: 3-3'-X-3'-SEQ ID NO: 3-5'); 5'-CTGTR'GTTCTC-X-CTCTTGR'TGTC-5' (5'-SEQ ID NO: 4-3'-X-3'-SEQ ID NO: 4-5'); 5'-CTGTR'GTTCU$_1$C$_1$-X-C$_1$U$_1$CTTGR'TGTC-5' (5'-SEQ ID NO: 5-3'-X-3'-SEQ ID NO: 5-5'); 5'-CTGTR'GTTC$_1$U$_1$C$_1$-X-C$_1$U$_1$C$_1$TTGR'TGTC-5' (5'-SEQ ID NO: 6-3'-X-3'-SEQ ID NO: 6-5'); 5'-TCTGTR'GTTCT-X-CGTTCGAACGT-5' (5'-SEQ ID NO: 7-3'-X-3'-SEQ ID NO: 17-5'); 5'-TCTGTR'GACAG-X-GACAGR'TGTCT-5' (5'-SEQ ID NO: 8-3'-X-3'-SEQ ID NO: 8-5'); 5'-TCTGTR'GACA$_1$G$_1$-X-G$_1$A$_1$CAGR'TGTCT-5' (5'-SEQ ID NO: 9-3'-X-3'-SEQ ID NO: 9-5'); 5'-TCAGTR'GTTAG-X-GATTGR'TGACT-5' (5'-SEQ ID NO: 10-3'-X-3'-SEQ ID NO: 10-5'); 5'-TCAGTR'GACTG-X-GTCAGR'TGACT-5' (5'-SEQ ID NO: 11-3'-X-3'-SEQ ID NO: 11-5'); 5'-TR'GTR'GAR'GAT-X-TAGR'AGR'TGR'T-5' (5'-SEQ ID NO: 12-3'-X-3'-SEQ ID NO: 12-5'); 5'-TR'GTR'GTAGTA-X-ATGATGR'TGR'T-5' (5'-SEQ ID NO: 13-3'-X-3'-SEQ ID NO: 13-5'); 5'-TR'GAAR'GTTCT-X-TCTTGR'AAGR'T-5' (5'-SEQ ID NO: 14-3'-X-3'-SEQ ID NO: 14-5'); and 5'-TR'GTAR'GTACT-X-TCATGR'ATGR'T-5' (5'-SEQ ID NO: 15-3'-X-3'-SEQ ID NO: 15-5'); 5'-TCRAACRTTCR-X-RCTTRCAARCT-5' (5'-SEQ ID NO: 16-3'-X-3'-SEQ ID NO: 16-5'), wherein R'=1-(2'-deoxy-β-D-ribofuranosyl)-2-oxo-7-deaza-8-methyl-purine; $A_1/C_1/G_1/U_1$=2'-O-methyl-ribonucleotides; R=2'-deoxy-7-deazaguanosine and X=glycerol linker.

In a fourth aspect the invention provides a method for therapeutically treating a vertebrate having cancer, an autoimmune disorder, airway inflammation, inflammatory disorders, skin disorders, allergy, asthma or a disease caused by a pathogen, such method comprising administering to the patient an immunostimulatory oligonucleotide having a structure from the group of 5'-TCTGTR'GTTCT-X-TCTTGR'TGTCT-5' (5'-SEQ ID NO: 1-3'-X-3'-SEQ ID NO: 1-5'); 5'-TCTGTR'GTTC$_1$U$_1$-X-U$_1$C$_1$TTGR'TGTCT-5' (5'-SEQ ID NO: 3-3'-X-3'-SEQ ID NO: 3-5'); 5'-CTGTR'GTTCTC-X-CTCTTGR'TGTC-5' (5'-SEQ ID NO: 4-3'-X-3'-SEQ ID NO: 4-5'); 5'-CTGTR'GTTCU$_1$C$_1$-X-C$_1$U$_1$CTTGR'TGTC-5' (5'-SEQ ID NO: 5-3'-X-3'-SEQ ID NO: 5-5'); 5'-CTGTR'GTTC$_1$U$_1$C$_1$-X-C$_1$U$_1$C$_1$TTGR'TGTC-5' (5'-SEQ ID NO: 6-3'-X-3'-SEQ ID NO: 6-5'); 5'-TCTGTR'GTTCT-X-CGTTCGAACGT-5' (5'-SEQ ID NO: 7-3'-X-3'-SEQ ID NO: 17-5'); 5'-TCTGTR'GACAG-X-GACAGR'TGTCT-5'(5'-SEQ ID NO: 8-3'-X-3'-SEQ ID NO: 8-5'); 5'-TCTGTR'GACA$_1$G$_1$-X-G$_1$A$_1$CAGR'TGTCT-5' (5'-SEQ ID NO: 9-3'-X-3'-SEQ ID NO: 9-5'); 5'-TCAGTR'GTTAG-X-GATTGR'TGACT-5' (5'-SEQ ID NO: 10-3'-X-3'-SEQ ID NO: 10-5'); 5'-TCAGTR'GACTG-X-GTCAGR'TGACT-5' (5'-SEQ ID NO: 11-3'-X-3'-SEQ ID NO: 11-5'); 5'-TR'GTR'GAR'GAT-X-TAGR'AGR'TGR'T-5' (5'-SEQ ID NO: 12-3'-X-3'-SEQ ID NO: 12-5'); 5'-TR'GTR'GTAGTA-X-ATGATGR'TGR'T-5' (5'-SEQ ID NO: 13-3'-X-3'-SEQ ID NO: 13-5'); 5'-TR'GAAR'GTTCT-X-TCTTGR'AAGR'T-5' (5'-SEQ ID NO: 14-3'-X-3'-SEQ ID NO: 14-5'); and 5'-TR'GTAR'GTACT-X-TCATGR'ATGR'T-5' (5'-SEQ ID NO: 15-3'-X-3'-SEQ ID NO: 15-5'); 5'-TCRAACRTTCR-X-RCTTRCAARCT-5' (5'-SEQ ID NO: 16-3'-X-3'-SEQ ID NO: 16-5'), wherein R'=1-(2'-deoxy-β-D-ribofuranosyl)-2-oxo-7-deaza-8-methyl-purine; $A_1/C_1/G_1/U_1$=2'-O-methyl-ribonucleotides; R=2'-deoxy-7-deazaguanosine and X=glycerol linker.

In a fifth aspect the invention provides a method for preventing cancer, an autoimmune disorder, airway inflammation, inflammatory disorders, skin disorders, allergy, asthma or a disease caused by a pathogen in a vertebrate, such method comprising administering to the vertebrate an immunostimulatory oligonucleotide having a structure from the group of 5'-TCTGTR'GTTCT-X-TCTTGR'TGTCT-5' (5'-SEQ ID NO: 1-3'-X-3'-SEQ ID NO: 1-5'); 5'-TCTGTR'GTTC$_1$U$_1$-X-U$_1$C$_1$TTGR'TGTCT-5' (5'-SEQ ID NO: 3-3'-X-3'-SEQ ID NO: 3-5'); 5'-CTGTR'GTTCTC-X-CTCTTGR'TGTC-5' (5'-SEQ ID NO: 4-3'-X-3'-SEQ ID NO: 4-5'); 5'-CTGTR'GTTCU$_1$C$_1$-X-C$_1$U$_1$CTTGR'TGTC-5' (5'-SEQ ID NO: 5-3'-X-3'-SEQ ID NO: 5-5'); 5'-CTGTR'GTTC$_1$U$_1$C$_1$-X-C$_1$U$_1$C$_1$TTGR'TGTC-5' (5'-SEQ ID NO: 6-3'-X-3'-SEQ ID NO: 6-5'); 5'-TCTGTR'GTTCT-X-CGTTCGAACGT-5' (5'-SEQ ID NO: 7-3'-X-3'-SEQ ID NO: 17-5'); 5'-TCTGTR'GACAG-X-GACAGR'TGTCT-5' (5'-SEQ ID NO: 8-3'-X-3'-SEQ ID NO: 8-5'); 5'-TCTGTR'GACA$_1$G$_1$-X-G$_1$A$_1$CAGR'TGTCT-5' (5'-SEQ ID NO: 9-3'-X-3'-SEQ ID NO: 9-5'); 5'-TCAGTR'GTTAG-X-GATTGR'TGACT-5' (5'-SEQ ID NO: 10-3'-X-3'-SEQ ID NO: 10-5'); 5'-TCAGTR'GACTG-X-GTCAGR'TGACT-5' (5'-SEQ ID NO: 11-3'-X-3'-SEQ ID NO: 11-5'); 5'-TR'GTR'GAR'GAT-X-TAGR'AGR'TGR'T-5' (5'-SEQ ID NO: 12-3'-X-3'-SEQ ID NO: 12-5'); 5'-TR'GTR'GTAGTA-X-ATGATGR'TGR'T-5' (5'-SEQ ID NO: 13-3'-X-3'-SEQ ID NO: 13-5'); 5'-TR'GAAR'GTTCT-X-TCTTGR'AAGR'T-5' (5'-SEQ ID NO: 14-3'-X-3'-SEQ ID NO: 14-5'); and 5'-TR'GTAR'GTACT-X-TCATGR'ATGR'T-5' (5'-SEQ ID NO: 15-3'-X-3'-SEQ ID NO: 15-5'); 5'-TCRAACRTTCR-X-RCTTRCAARCT-5' (5'-SEQ ID NO: 16-3'-X-3'-SEQ ID NO: 16-5'), wherein R'=1-(2'-deoxy-β-D-ribofuranosyl)-2-oxo-7-deaza-8-methyl-purine; $A_1/C_1/G_1/U_1$=2'-O-methyl-ribonucleotides; R=2'-deoxy-7-deazaguanosine and X=glycerol linker.

DETAILED DESCRIPTION OF THE PREFERRED EMBODIMENTS

Figure 1:
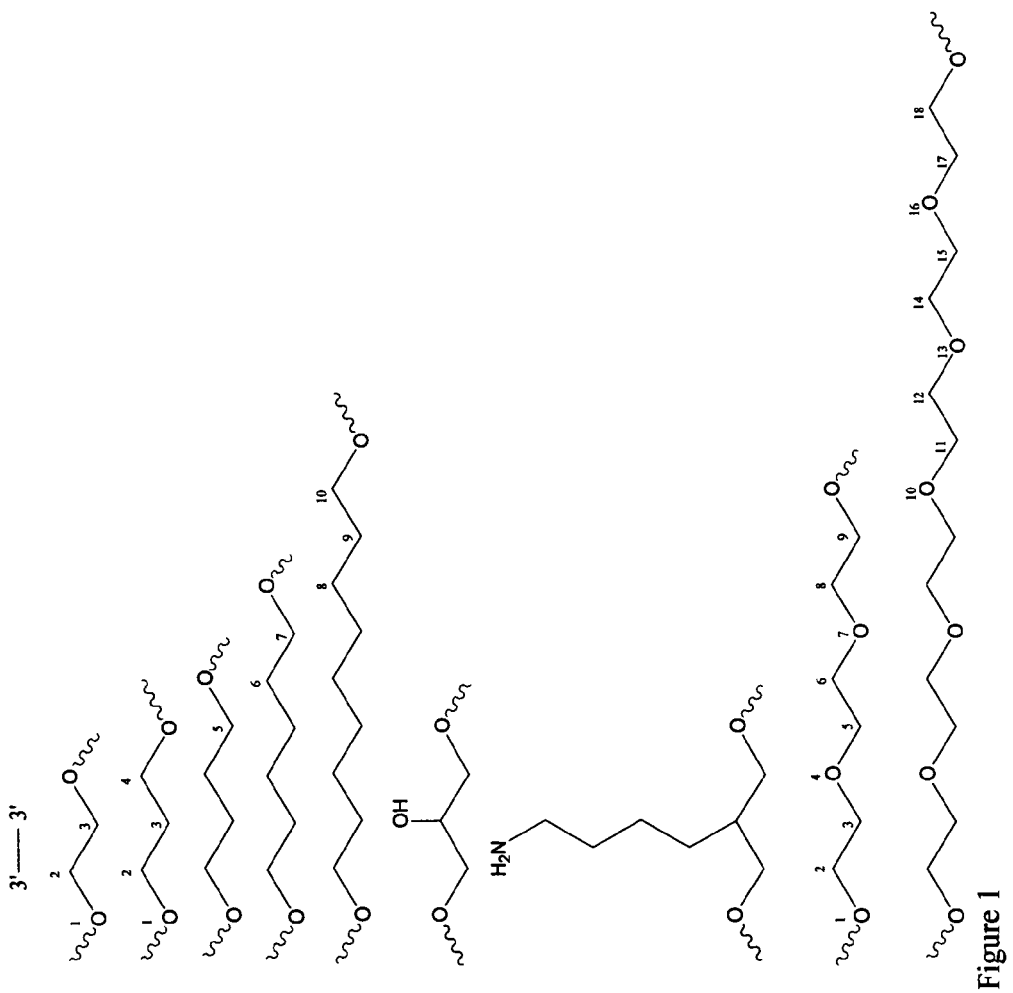
FIG. 1 depicts a group of representative small molecule linkers suitable for linear synthesis of immunostimulatory oligonucleotides of the invention.
Figure 2:
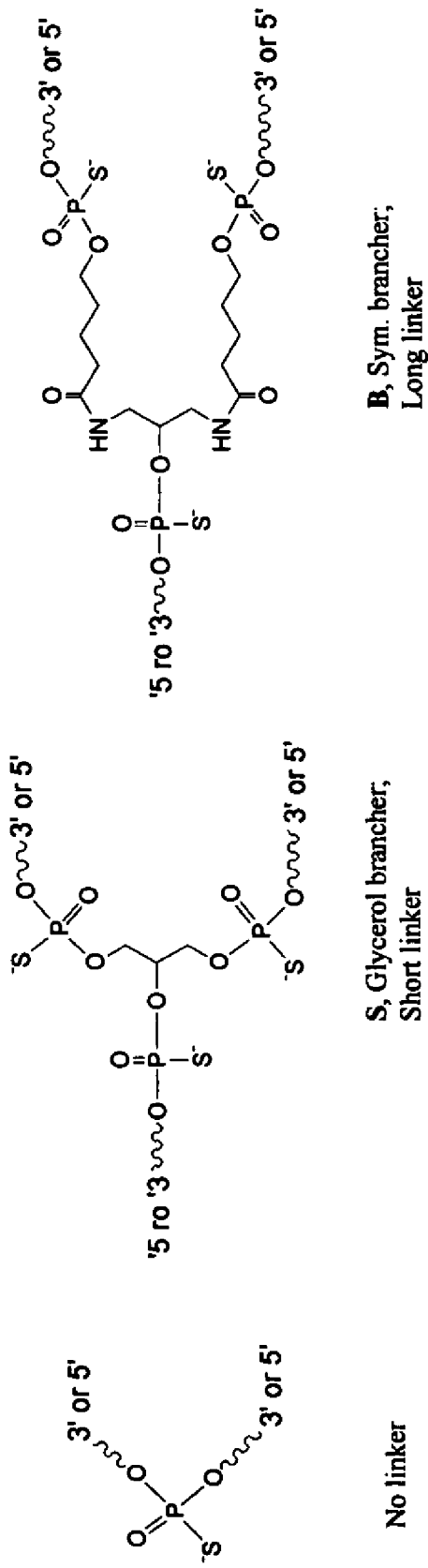
FIG. 2 depicts a group of representative small molecule linkers suitable for parallel synthesis of immunostimulatory oligonucleotides of the invention.

The invention relates to the therapeutic use of oligonucleotides as immunostimulatory agents for immunotherapy applications. The issued patents, patent applications, and references that are cited herein are hereby incorporated by reference to the same extent as if each was specifically and individually indicated to be incorporated by reference. In the event of inconsistencies between any teaching of any reference cited herein and the present specification, the latter shall prevail for purposes of the invention.

The invention provides methods for enhancing the immune response caused by immunostimulatory compounds used for immunotherapy applications such as, but not limited to, treatment of cancer, autoimmune disorders, asthma, respiratory allergies, food allergies, and bacteria, parasitic, and viral infections in adult and pediatric human and veterinary applications. Thus, the invention further provides compounds having optimal levels of immunostimulatory effect for immunotherapy and methods for making and using such compounds. In addition, compounds of the invention are useful as adjuvants in combination with DNA vaccines, antibodies, and allergens; and in combination with chemotherapeutic agents and/or antisense oligonucleotides.

The present inventors have surprisingly discovered that modification of an immunostimulatory oligonucleotide to optimally present its 5' ends dramatically affects its immunostimulatory capabilities. In addition, the present inventors have discovered that the cytokine profile and species specificity of an immune response can be modulated by using novel purine or pyrimidine structures as part of an immunostimulatory oligonucleotide.

In a first aspect, the invention provides immunostimulatory oligonucleotides alone or comprising at least two oligonucleotides linked at their 3' ends, or an internucleoside linkage or a functionalized nucleobase or sugar to a non-nucleotidic linker, at least one of the oligonucleotides being an immunostimulatory oligonucleotide and having an accessible 5' end. As used herein, the term "accessible 5' end" means that the 5' end of the oligonucleotide is sufficiently available such that the factors that recognize and bind to oligonucleotide and stimulate the immune system have access to it. In oligonucleotides having an accessible 5' end, the 5' OH position of the terminal sugar is not covalently linked to more than two nucleoside residues or any other moiety that interferes with interaction with the 5' end. Optionally, the 5' OH can be linked to a phosphate, phosphorothioate, or phosphorodithioate moiety, an aromatic or aliphatic linker, cholesterol, or another entity which does not interfere with accessibility. The immunostimulatory oligonucleotides according to the invention preferably further comprise an immunostimulatory dinucleotide comprising a novel purine or pyrimidine.

In certain embodiments, the immunostimulatory oligonucleotides include a ribozyme or a decoy oligonucleotide. As used herein, the term "ribozyme" refers to an oligonucleotide that possesses catalytic activity. Preferably, the ribozyme binds to a specific nucleic acid target and cleaves the target. As used herein, the term "decoy oligonucleotide" refers to an oligonucleotide that binds to a transcription factor in a sequence-specific manner and arrests transcription activity. Preferably, the ribozyme or decoy oligonucleotide exhibits secondary structure, including, without limitation, stem-loop or hairpin structures. In certain embodiments, at least one oligonucleotide comprises poly(I)-poly(C). In certain embodiments, at least one set of Nn includes a string of 3 to 10 dGs and/or Gs or 2'-substituted ribo or arabino Gs.

For purposes of the invention, the term "oligonucleotide" refers to a polynucleoside formed from a plurality of linked nucleoside units. Such oligonucleotides can be obtained from existing nucleic acid sources, including genomic or cDNA, but are preferably produced by synthetic methods. In preferred embodiments each nucleoside unit includes a heterocyclic base and a pentofuranosyl, trehalose, arabinose, 2'-deoxy-2'-substituted arabinose, 2'-O-substituted arabinose or hexose sugar group. The nucleoside residues can be coupled to each other by any of the numerous known internucleoside linkages. Such internucleoside linkages include, without limitation, phosphodiester, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide" also encompasses polynucleosides having one or more stereospecific internucleoside linkage (e.g., ($R_P$)- or ($S_P$)-phosphorothioate, alkylphosphonate, or phosphotriester linkages). As used herein, the terms "oligonucleotide" and "dinucleotide" are expressly intended to include polynucleosides and dinucleosides having any such internucleoside linkage, whether or not the linkage comprises a phosphate group. In certain preferred embodiments, these internucleoside linkages may be phosphodiester, phosphorothioate, or phosphorodithioate linkages, or combinations thereof.

In some embodiments, the oligonucleotides each have from about 3 to about 35 nucleoside residues, preferably from about 4 to about 30 nucleoside residues, more preferably from about 4 to about 20 nucleoside residues. In some embodiments, the immunostimulatory oligonucleotides comprise oligonucleotides have from about 5 to about 18, or from about 5 to about 14, nucleoside residues. As used herein, the term "about" implies that the exact number is not critical. Thus, the number of nucleoside residues in the oligonucleotides is not critical, and oligonucleotides having one or two fewer nucleoside residues, or from one to several additional nucleoside residues are contemplated as equivalents of each of the embodiments described above. In some embodiments, one or more of the oligonucleotides have 11 nucleotides. In the context of immunostimulatory oligonucleotides, preferred embodiments have from about 13 to about 35 nucleotides, more preferably from about 13 to about 26 nucleotides.

The term "oligonucleotide" also encompasses polynucleosides having additional substituents including, without limitation, protein groups, lipophilic groups, intercalating agents, diamines, folic acid, cholesterol and adamantane. The term "oligonucleotide" also encompasses any other nucleobase containing polymer, including, without limitation, peptide nucleic acids (PNA), peptide nucleic acids with phosphate groups (PHONA), locked nucleic acids (LNA), morpholino-backbone oligonucleotides, and oligonucleotides having backbone sections with alkyl linkers or amino linkers.

The oligonucleotides of the invention can include naturally occurring nucleosides, modified nucleosides, or mixtures thereof. As used herein, the term "modified nucleoside" is a nucleoside that includes a modified heterocyclic base, a modified sugar moiety, or a combination thereof. In some embodiments, the modified nucleoside is a non-natural pyrimidine or purine nucleoside, as herein described. In some embodiments, the modified nucleoside is a 2'-substituted ribonucleoside an arabinonucleoside or a 2'-deoxy-2'-substituted-arabinoside.

For purposes of the invention, the term "2'-substituted ribonucleoside" or "2'-substituted arabinoside" includes ribonucleosides or arabinonucleoside in which the hydroxyl group at the 2' position of the pentose moiety is substituted to produce a 2'-substituted or 2'-O-substituted ribonucleoside. Preferably, such substitution is with a lower alkyl group containing 1-6 saturated or unsaturated carbon atoms, or with an aryl group having 6-10 carbon atoms, wherein such alkyl, or aryl group may be unsubstituted or may be substituted, e.g., with halo, hydroxy, trifluoromethyl, cyano, nitro, acyl, acyloxy, alkoxy, carboxyl, carboalkoxy, or amino groups. Examples of 2'-O-substituted ribonucleosides or 2'-O-substituted-arabinosides include, without limitation 2'-O-methylribonucleosides or 2'-O-methylarabinosides and 2'-O-methoxyethylribonucleosides or 2'-O-methoxyethylarabinosides.

The term "2'-substituted ribonucleoside" or "2'-substituted arabinoside" also includes ribonucleosides or arabinonucleosides in which the 2'-hydroxyl group is replaced with a lower alkyl group containing 1-6 saturated or unsaturated carbon atoms, or with an amino or halo group. Examples of such 2'-substituted ribonucleosides or 2'-substituted arabinosides include, without limitation, 2'-amino, 2'-fluoro, 2'-allyl, and 2'-propargyl ribonucleosides or arabinosides.

The term "oligonucleotide" includes hybrid and chimeric oligonucleotides. A "chimeric oligonucleotide" is an oligonucleotide having more than one type of internucleoside linkage. One preferred example of such a chimeric oligonucleotide is a chimeric oligonucleotide comprising a phosphorothioate, phosphodiester or phosphorodithioate region and non-ionic linkages such as alkylphosphonate or alkylphosphonothioate linkages (see e.g., Pederson et al. U.S. Pat. Nos. 5,635,377 and 5,366,878).

A "hybrid oligonucleotide" is an oligonucleotide having more than one type of nucleoside. One preferred example of such a hybrid oligonucleotide comprises a ribonucleotide or 2'-substituted ribonucleotide region, and a deoxyribonucleotide region (see, e.g., Metelev and Agrawal, U.S. Pat. Nos. 5,652,355, 6,346,614 and 6,143,881).

For purposes of the invention, the term "immunostimulatory oligonucleotide" refers to an oligonucleotide as described above that induces an immune response when administered to a vertebrate, such as a fish, fowl, or mammal. As used herein, the term "mammal" includes, without limitation rats, mice, cats, dogs, horses, cattle, cows, pigs, rabbits, non-human primates, and humans. Useful immunostimulatory oligonucleotides can be found described in Agrawal et al., WO 98/49288, published Nov. 5, 1998; WO 01/12804, published Feb. 22, 2001; WO 01/55370, published Aug. 2, 2001; PCT/US01/13682, filed Apr. 30, 2001; and PCT/US01/30137, filed Sep. 26, 2001. Preferably, the immunostimulatory oligonucleotide comprises at least one phosphodiester, phosphorothioate, or phosphorodithioate internucleoside linkage.

In some embodiments, the immunostimulatory oligonucleotide comprises an immunostimulatory dinucleotide of formula 5'-Pyr-Pur-3', wherein Pyr is a natural or synthetic pyrimidine nucleoside and Pur is a natural or synthetic purine nucleoside. In some preferred embodiments, the immunostimulatory oligonucleotide comprises an immunostimulatory dinucleotide of formula 5'-Pur*-Pur-3', wherein Pur* is a synthetic purine nucleoside and Pur is a natural or synthetic purine nucleoside. In various places the dinucleotide is expressed as RpG, C*pG or YZ, in which case respectively, R, C*, or Y represents a synthetic purine. A particularly preferred synthetic purine is 2-oxo-7-deaza-8-methyl-purine. When this synthetic purine is in the Pur* position of the dinucleotide, species-specificity (sequence dependence) of the immunostimulatory effect is overcome and cytokine profile is improved. As used herein, the term "pyrimidine nucleoside" refers to a nucleoside wherein the base component of the nucleoside is a monocyclic nucleobase. Similarly, the term "purine nucleoside" refers to a nucleoside wherein the base component of the nucleoside is a bicyclic nucleobase. For purposes of the invention, a "synthetic" pyrimidine or purine nucleoside includes a non-naturally occurring pyrimidine or purine base, a non-naturally occurring sugar moiety, or a combination thereof.

Preferred pyrimidine nucleosides according to the invention have the structure (I):

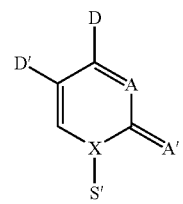

wherein:

D is a hydrogen bond donor;

D' is selected from the group consisting of hydrogen, hydrogen bond donor, hydrogen bond acceptor, hydrophilic group, hydrophobic group, electron withdrawing group and electron donating group;

A is a hydrogen bond acceptor or a hydrophilic group;

A' is selected from the group consisting of hydrogen bond acceptor, hydrophilic group, hydrophobic group, electron withdrawing group and electron donating group;

X is carbon or nitrogen; and

S' is a pentose or hexose sugar ring, or a non-naturally occurring sugar.

Preferably, the sugar ring is derivatized with a phosphate moiety, modified phosphate moiety, or other linker moiety suitable for linking the pyrimidine nucleoside to another nucleoside or nucleoside analog.

Preferred hydrogen bond donors include, without limitation, —NH—, —NH$_2$, —SH and —OH. Preferred hydrogen bond acceptors include, without limitation, C=O, C=S, and the ring nitrogen atoms of an aromatic heterocycle, e.g., N3 of cytosine.

In some embodiments, the base moiety in (I) is a non-naturally occurring pyrimidine base. Examples of preferred non-naturally occurring pyrimidine bases include, without limitation, 5-hydroxycytosine, 5-hydroxymethylcytosine, N4-alkylcytosine, preferably N4-ethylcytosine, and 4-thiouracil. However, in some embodiments 5-bromocytosine is specifically excluded.

In some embodiments, the sugar moiety S' in (I) is a non-naturally occurring sugar moiety. For purposes of the present invention, a "naturally occurring sugar moiety" is a sugar moiety that occurs naturally as part of nucleic acid, e.g., ribose and 2'-deoxyribose, and a "non-naturally occurring sugar moiety" is any sugar that does not occur naturally as part of a nucleic acid, but which can be used in the backbone for an oligonucleotide, e.g, hexose. Arabinose and arabinose derivatives are examples of preferred sugar moieties.

Preferred purine nucleoside analogs according to the invention have the structure (II):

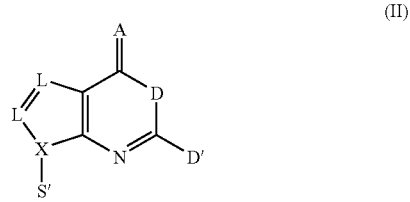

(II)

wherein:
D is a hydrogen bond donor;
D' is selected from the group consisting of hydrogen, hydrogen bond donor, and hydrophilic group;
A is a hydrogen bond acceptor or a hydrophilic group;
X is carbon or nitrogen;
each L is independently an atom selected from the group consisting of C, O, N and S; and
S' is a pentose or hexose sugar ring, or a non-naturally occurring sugar.

Preferably, the sugar ring is derivatized with a phosphate moiety, modified phosphate moiety, or other linker moiety suitable for linking the pyrimidine nucleoside to another nucleoside or nucleoside analog.

Preferred hydrogen bond donors include, without limitation, —NH—, —NH$_2$, —SH and —OH. Preferred hydrogen bond acceptors include, without limitation, C=O, C=S, —NO$_2$ and the ring nitrogen atoms of an aromatic heterocycle, e.g., N1 of guanine.

In some embodiments, the base moiety in (II) is a non-naturally occurring purine base. Examples of preferred non-naturally occurring purine bases include, without limitation, 2-amino-6-thiopurine and 2-amino-6-oxo-7-deazapurine. In some embodiments, the sugar moiety S' in (II) is a naturally occurring sugar moiety, as described above for structure (I).

In preferred embodiments, the immunostimulatory dinucleotide is selected from the group consisting of CpG, C*pG, CpG*, and C*pG*, wherein the base of C is cytosine, the base of C* is 2'-thymine, 5-hydroxycytosine, N4-alkyl-cytosine, 4-thiouracil or other non-natural pyrimidine, or 2-oxo-7-deaza-8-methylpurine, wherein when the base is 2-oxo-7-deaza-8-methyl-purine, it is preferably covalently bound to the 1'-position of a pentose via the 1 position of the base; the base of G is guanosine, the base of G* is 2-amino-6-oxo-7-deazapurine, 2-oxo-7-deaza-8-methylpurine, 6-thioguanine, 6-oxopurine, or other non-natural purine nucleoside, and p is an internucleoside linkage selected from the group consisting of phosphodiester, phosphorothioate, and phosphorodithioate. In certain preferred embodiments, the immunostimulatory dinucleotide is not CpG.

The immunostimulatory oligonucleotides may include immunostimulatory moieties on one or both sides of the immunostimulatory dinucleotide. Thus, in some embodiments, the immunostimulatory oligonucleotide comprises an immunostimulatory domain of structure (III):

5'-Nn-N1-Y-Z-N1-Nn-3'  (III)

wherein:
the base of Y is cytosine, thymine, 5-hydroxycytosine, N4-alkyl-cytosine, 4-thiouracil or other non-natural pyrimidine nucleoside, or 2-oxo-7-deaza-8 methyl purine, wherein when the base is 2-oxo-7-deaza-8-methyl-purine, it is preferably covalently bound to the 1'-position of a pentose via the 1 position of the base;
the base of Z is guanine, 2-amino-6-oxo-7-deazapurine, 2-oxo-7deaza-8-methylpurine, 2-amino-6-thio-purine, 6-oxopurine or other non-natural purine nucleoside;
N1 and Nn, independent at each occurrence, is preferably a naturally occurring or a synthetic nucleoside or an immunostimulatory moiety selected from the group consisting of abasic nucleosides, arabinonucleosides, 2'-deoxyuridine, α-deoxyribonucleosides, β-L-deoxyribonucleosides, and nucleosides linked by a phosphodiester or modified internucleoside linkage to the adjacent nucleoside on the 3' side, the modified internucleotide linkage being selected from, without limitation, a linker having a length of from about 2 angstroms to about 200 angstroms, C2-C18 alkyl linker, poly (ethylene glycol) linker, 2-aminobutyl-1,3-propanediol linker, glyceryl linker, 2'-5' internucleoside linkage, and phosphorothioate, phosphorodithioate, or methylphosphonate internucleoside linkage;
provided that at least one N1 or Nn is optionally an immunostimulatory moiety;
wherein n is a number from 0 to 30; and
wherein the 3'end, an internucleoside linker, or a derivatized nucleobase or sugar is linked directly or via a non-nucleotidic linker to another oligonucleotide, which may or may not be immunostimulatory.

In some preferred embodiments, YZ is arabinocytidine or 2'-deoxy-2'-substituted arabinocytidine and arabinoguanosine or 2'deoxy-2'-substituted arabinoguanosine. Preferred immunostimulatory moieties include natural phosphodiester backbones and modifications in the phosphate backbones, including, without limitation, methylphosphonates, methylphosphonothioates, phosphotriesters, phosphothiotriesters, phosphorothioates, phosphorodithioates, triester prodrugs, sulfones, sulfonamides, sulfamates, formacetal, N-methylhydroxylamine, carbonate, carbamate, morpholino, boranophosphonate, phosphoramidates, especially primary amino-phosphoramidates, N3 phosphoramidates and N5 phosphoramidates, and stereospecific linkages (e.g., (R$_P$)- or (S$_P$)-phosphorothioate, alkylphosphonate, or phosphotriester linkages).

Preferred immunostimulatory moieties according to the invention further include nucleosides having sugar modifications, including, without limitation, 2'-substituted pentose sugars including, without limitation, 2'-O-methylribose, 2'-O-methoxyethylribose, 2'-O-propargylribose, and 2'-deoxy-2'-fluororibose; 3'-substituted pentose sugars, including, without limitation, 3'-O-methylribose; 1',2'-dideoxyribose; arabinose; substituted arabinose sugars, including, without limitation, 1'-methylarabinose, 3'-hydroxymethylarabinose, 4'-hydroxymethylarabinose, 3'-hydroxyarabinose and 2'-substituted arabinose sugars; hexose sugars, including, without limitation, 1,5-anhydrohexitol; and alpha-anomers. In embodiments in which the modified sugar is a 3'-deoxyribonucleoside or a 3'-O-substituted ribonucleoside, the immunostimulatory moiety is attached to the adjacent nucleoside by way of a 2'-5' internucleoside linkage.

Preferred immunostimulatory moieties according to the invention further include oligonucleotides having other carbohydrate backbone modifications and replacements, including peptide nucleic acids (PNA), peptide nucleic acids with phosphate groups (PHONA), locked nucleic acids (LNA), morpholino backbone oligonucleotides, and oligonucleotides having backbone linker sections having a length of from about 2 angstroms to about 200 angstroms, including without limitation, alkyl linkers or amino linkers. The alkyl linker may be branched or unbranched, substituted or unsubstituted, and chirally pure or a racemic mixture. Most preferably, such alkyl linkers have from about 2 to about 18 carbon atoms. In some preferred embodiments such alkyl linkers have from about 3 to about 9 carbon atoms. Some alkyl linkers include one or more functional groups selected from the group consisting of hydroxy, amino, thiol, thioether, ether, amide, thioamide, ester, urea, and thioether. Some such functionalized alkyl linkers are poly(ethylene glycol) linkers of formula —O—(CH$_2$—CH$_2$—O—)$_n$, (n=1-9). Some other functionalized alkyl linkers are peptides or amino acids.

Preferred immunostimulatory moieties according to the invention further include DNA isoforms, including, without limitation, β-L-deoxyribonucleosides and α-deoxyribonucleosides. Preferred immunostimulatory moieties according to the invention incorporate 3' modifications, and further include nucleosides having unnatural internucleoside linkage positions, including, without limitation, 2'-5', 2'-2', 3'-3' and 5'-5' linkages.

Preferred immunostimulatory moieties according to the invention further include nucleosides having modified heterocyclic bases, including, without limitation, 5-hydroxycytosine, 5-hydroxymethylcytosine, N4-alkylcytosine, preferably N4-ethylcytosine, 4-thiouracil, 6-thioguanine, 7-deazaguanine, inosine, nitropyrrole, C5-propynylpyrimidine, and diaminopurines, including, without limitation, 2,6-diaminopurine.

By way of specific illustration and not by way of limitation, for example, in the immunostimulatory domain of structure (III), a methylphosphonate internucleoside linkage at position N1 or Nn is an immunostimulatory moiety, a linker having a length of from about 2 angstroms to about 200 angstroms, C2-C18 alkyl linker at position X1 is an immunostimulatory moiety, and a β-L-deoxyribonucleoside at position X1 is an immunostimulatory moiety. See Table 1 below for representative positions and structures of immunostimulatory moieties. It is to be understood that reference to a linker as the immunostimulatory moiety at a specified position means that the nucleoside residue at that position is substituted at its 3'-hydroxyl with the indicated linker, thereby creating a modified internucleoside linkage between that nucleoside residue and the adjacent nucleoside on the 3' side. Similarly, reference to a modified internucleoside linkage as the immunostimulatory moiety at a specified position means that the nucleoside residue at that position is linked to the adjacent nucleoside on the 3' side by way of the recited linkage.

TABLE 1

| Position | TYPICAL IMMUNOSTIMULATORY MOIETIES |
|---|---|
| N1 | Naturally-occurring nucleosides, abasic nucleoside, arabinonucleoside, 2'-deoxyuridine, β-L-deoxyribonucleoside C2-C18 alkyl linker, poly(ethylene glycol) linkage, 2-aminobutyl-1,3-propanediol linker (amino linker), 2'-5' internucleoside linkage, methylphosphonate internucleoside linkage |
| Nn | Naturally-occurring nucleosides, abasic nucleoside, arabinonucleosides, 2'-deoxyuridine, 2'-O-substituted ribonucleoside, 2'-5' internucleoside linkage, methylphosphonate internucleoside linkage, provided that N1 and N2 cannot both be abasic linkages |

Table 2 shows representative positions and structures of immunostimulatory moieties within an immunostimulatory oligonucleotide having an upstream potentiation domain. As used herein, the term "Spacer 9" refers to a poly(ethylene glycol) linker of formula —O—(CH$_2$CH$_2$—O)$_n$—, wherein n is 3. The term "Spacer 18" refers to a poly(ethylene glycol) linker of formula —O—(CH$_2$CH$_2$—O)$_n$—, wherein n is 6. As used herein, the term "C2-C18 alkyl linker refers to a linker of formula —O—(CH2)$_q$—O—, where q is an integer from 2 to 18. Accordingly, the terms "C3-linker" and "C3-alkyl linker" refer to a linker of formula —O—(CH$_2$)$_3$—O—. For each of Spacer 9, Spacer 18, and C2-C18 alkyl linker, the linker is connected to the adjacent nucleosides by way of phosphodiester, phosphorothioate, or phosphorodithioate linkages.

TABLE 2

| Position | TYPICAL IMMUNOSTIMULATORY MOIETY |
|---|---|
| 5' N2 | Naturally-occurring nucleosides, 2-aminobutyl-1,3-propanediol linker |
| 5' N1 | Naturally-occurring nucleosides, β-L-deoxyribonucleoside, C2-C18 alkyl linker, poly(ethylene glycol), abasic linker, 2-aminobutyl-1,3-propanediol linker |
| 3' N1 | Naturally-occurring nucleosides, 1',2'-dideoxyribose, 2'-O-methyl-ribonucleoside, C2-C18 alkyl linker, Spacer 9, Spacer 18 |
| 3' N2 | Naturally-occurring nucleosides, 1',2'-dideoxyribose, 3'-deoxyribonucleoside, β-L-deoxyribonucleoside, 2'-O-propargyl-ribonucleoside, C2-C18 alkyl linker, Spacer 9, Spacer 18, methylphosphonate internucleoside linkage |
| 3' N3 | Naturally-occurring nucleosides, 1',2'-dideoxyribose, C2-C18 alkyl linker, Spacer 9, Spacer 18, methylphosphonate internucleoside linkage, 2'-5' internucleoside linkage, d(G)n, polyI-polyC |
| 3'N2 + 3'N3 | 1',2'-dideoxyribose, β-L-deoxyribonucleoside, C2-C18 alkyl linker, d(G)n, polyI-polyC |
| 3'N3 + 3' N4 | 2'-O-methoxyethyl-ribonucleoside, methylphosphonate internucleoside linkage, d(G)n, polyI-polyC |
| 3'N5 + 3' N6 | 1',2'-dideoxyribose, C2-C18 alkyl linker, d(G)n, polyI-polyC |
| 5'N1 + 3' N3 | 1',2'-dideoxyribose, d(G)n, polyI-polyC |

Table 3 shows representative positions and structures of immunostimulatory moieties within an immunostimulatory oligonucleotide having a downstream potentiation domain.

TABLE 3

| Position | TYPICAL IMMUNOSTIMULATORY MOIETY |
|---|---|
| 5' N2 | methylphosphonate internucleoside linkage |
| 5' N1 | methylphosphonate internucleoside linkage |

TABLE 3-continued

| Position | TYPICAL IMMUNOSTIMULATORY MOIETY |
|---|---|
| 3' N1 | 1',2'-dideoxyribose, methylphosphonate internucleoside linkage, 2'-O-methyl |
| 3' N2 | 1',2'-dideoxyribose, β-L-deoxyribonucleoside, C2-C18 alkyl linker, Spacer 9, Spacer 18, 2-aminobutyl-1, 3-propanediol linker, methylphosphonate internucleoside linkage, 2'-O-methyl |
| 3' N3 | 3'-deoxyribonucleoside, 3'-O-substituted ribonucleoside, 2'-O-propargyl-ribonucleoside |
| 3'N2 + 3' N3 | 1',2'-dideoxyribose, β-L-deoxyribonucleoside |

The immunostimulatory oligonucleotides according to the invention comprise at least two oligonucleotides linked at their 3' ends or internucleoside linkage or a functionalized nucleobase or sugar via a non-nucleotidic linker. For purposes of the invention, a "non-nucleotidic linker" is any moiety that can be linked to the oligonucleotides by way of covalent or non-covalent linkages. Preferably such linker is from about 2 angstroms to about 200 angstroms in length. Several examples of preferred linkers are set forth below. Non-covalent linkages include, but are not limited to, electrostatic interaction, hydrophobic interactions, π-stacking interactions, and hydrogen bonding. The term "non-nucleotidic linker" is not meant to refer to an internucleoside linkage, as described above, e.g., a phosphodiester, phosphorothioate, or phosphorodithioate functional group, that directly connects the 3'-hydroxyl groups of two nucleosides. For purposes of this invention, such a direct 3'-3' linkage (no linker involved) is considered to be a "nucleotidic linkage."

In some embodiments, the non-nucleotidic linker is a metal, including, without limitation, gold particles. In some other embodiments, the non-nucleotidic linker is a soluble or insoluble biodegradable polymer bead.

Figure 5:
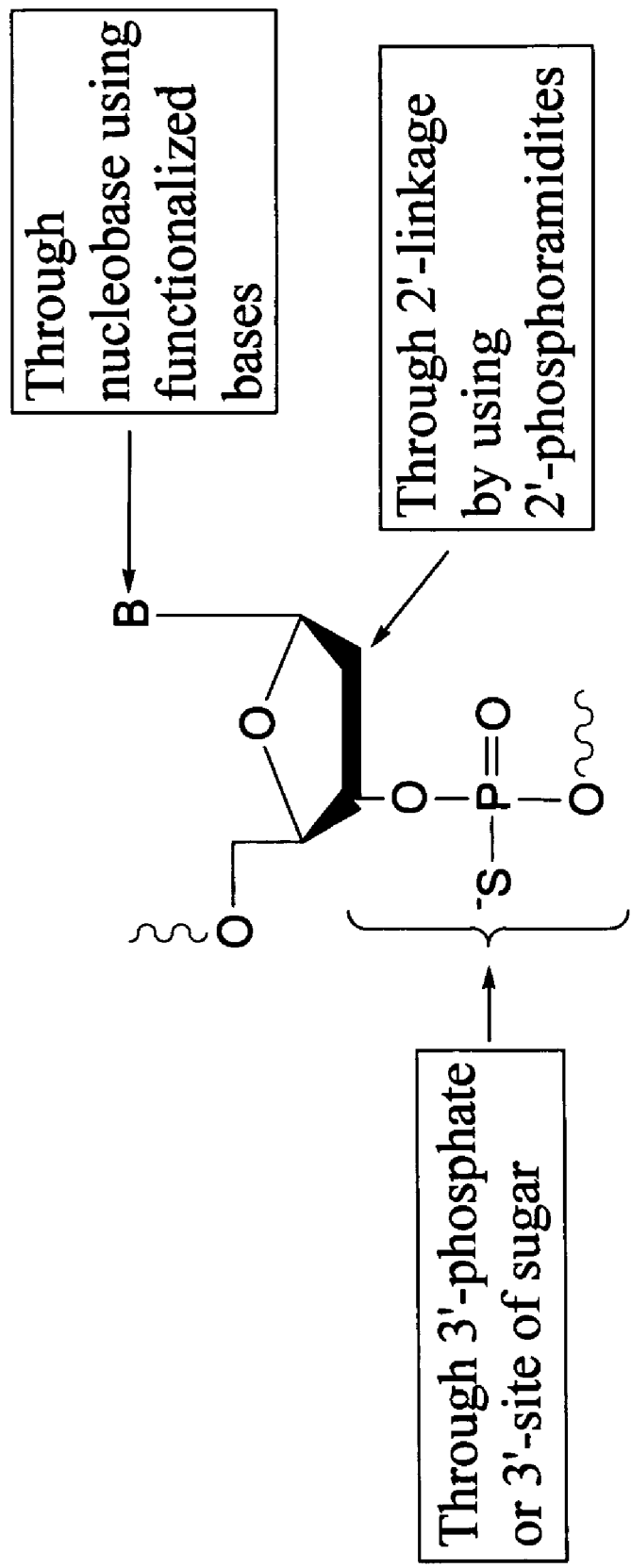
FIG. 5 is a schematic representation of the 3'-terminal nucleoside of an oligonucleotide, showing that a non-nucleotidic linkage can be attached to the nucleoside at the nucleobase, at the 3' position, or at the 2' position.

In yet other embodiments, the non-nucleotidic linker is an organic moiety having functional groups that permit attachment to the oligonucleotide. Such attachment preferably is by any stable covalent linkage. As a non-limiting example, the linker may be attached to any suitable position on the nucleoside, as illustrated in FIG. 5. In some preferred embodiments, the linker is attached to the 3'-hydroxyl. In such embodiments, the linker preferably comprises a hydroxyl functional group, which preferably is attached to the 3'-hydroxyl by means of a phosphodiester, phosphorothioate, phosphorodithioate or non-phosphate-based linkages.

In some embodiments, the non-nucleotidic linker is a biomolecule, including, without limitation, polypeptides, antibodies, lipids, antigens, allergens, and oligosaccharides. In some other embodiments, the non-nucleotidic linker is a small molecule. For purposes of the invention, a small molecule is an organic moiety having a molecular weight of less than 1,000 Da. In some embodiments, the small molecule has a molecular weight of less than 750 Da.

In some embodiments, the small molecule is an aliphatic or aromatic hydrocarbon, either of which optionally can include, either in the linear chain connecting the oligonucleotides or appended to it, one or more functional groups selected from the group consisting of hydroxy, amino, thiol, thioether, ether, amide, thioamide, ester, urea, and thiourea. The small molecule can be cyclic or acyclic. Examples of small molecule linkers include, but are not limited to, amino acids, carbohydrates, cyclodextrins, adamantane, cholesterol, haptens and antibiotics. However, for purposes of describing the non-nucleotidic linker, the term "small molecule" is not intended to include a nucleoside.

In some embodiments, the small molecule linker is glycerol or a glycerol homolog of the formula HO—$(CH_2)_o$—CH(OH)—$(CH_2)_p$—OH, wherein o and p independently are integers from 1 to about 6, from 1 to about 4, or from 1 to about 3. In some other embodiments, the small molecule linker is a derivative of 1,3-diamino-2-hydroxypropane. Some such derivatives have the formula HO—$(CH_2)_m$—C(O)NH—$CH_2$—CH(OH)—$CH_2$—NHC(O)—$(CH_2)_m$—OH, wherein m is an integer from 0 to about 10, from 0 to about 6, from 2 to about 6, or from 2 to about 4.

Some non-nucleotidic linkers according to the invention permit attachment of more than two oligonucleotides. For example, the small molecule linker glycerol has three hydroxyl groups to which oligonucleotides may be covalently attached. Some immunostimulatory oligonucleotides according to the invention, therefore, comprise more than two oligonucleotides linked at their 3' ends to a non-nucleotidic linker.

Figure 3:
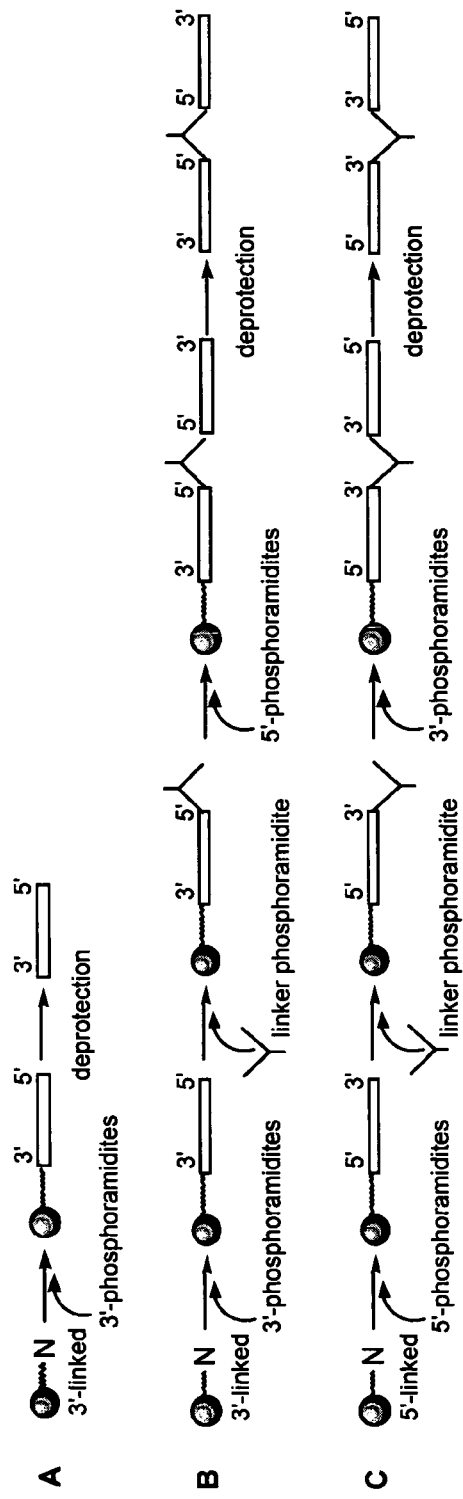
FIG. 3 is a synthetic scheme for the linear synthesis of immunostimulatory oligonucleotides of the invention. DMTr=4,4'-dimethoxytrityl; CE=cyanoethyl.
Figure 3:
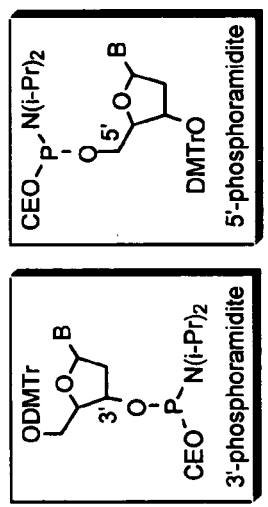
Figure 3:
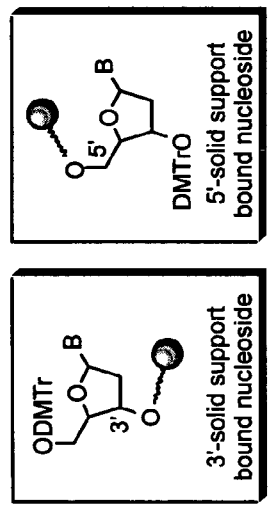
Figure 4:
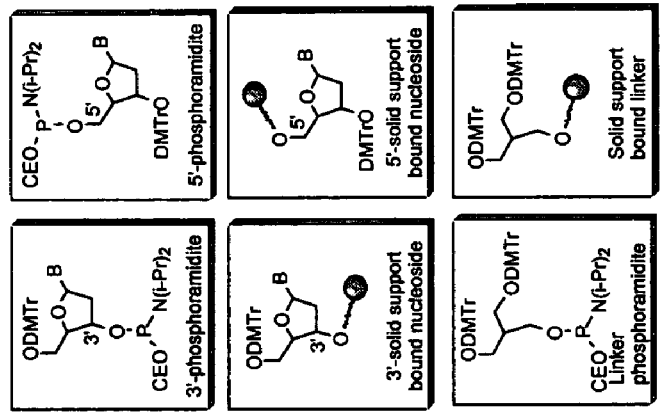
FIG. 4 is a synthetic scheme for the parallel synthesis of immunostimulatory oligonucleotides of the invention. DMTr=4,4'-dimethoxytrityl; CE=cyanoethyl.
Figure 4:
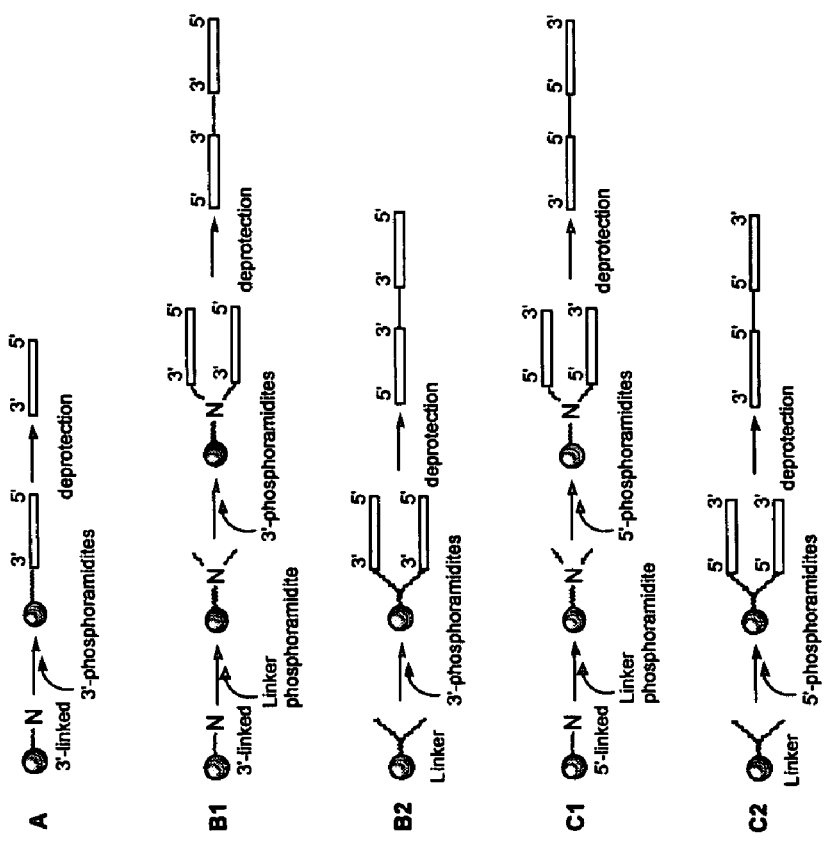

The immunostimulatory oligonucleotides of the invention may conveniently be synthesized using an automated synthesizer and phosphoramidite approach as schematically depicted in FIGS. 3 and 4, and further described in the Examples. In some embodiments, the immunostimulatory oligonucleotides are synthesized by a linear synthesis approach (see FIG. 3). As used herein, the term "linear synthesis" refers to a synthesis that starts at one end of the immunostimulatory oligonucleotide and progresses linearly to the other end. Linear synthesis permits incorporation of either identical or un-identical (in terms of length, base composition and/or chemical modifications incorporated) monomeric units into the immunostimulatory oligonucleotides.

An alternative mode of synthesis is "parallel synthesis", in which synthesis proceeds outward from a central linker moiety (see FIG. 4). A solid support attached linker can be used for parallel synthesis, as is described in U.S. Pat. No. 5,912,332. Alternatively, a universal solid support (such as phosphate attached controlled pore glass) support can be used.

Parallel synthesis of immunostimulatory oligonucleotides has several advantages over linear synthesis: (1) parallel synthesis permits the incorporation of identical monomeric units; (2) unlike in linear synthesis, both (or all) the monomeric units are synthesized at the same time, thereby the number of synthetic steps and the time required for the synthesis is the same as that of a monomeric unit; and (3) the reduction in synthetic steps improves purity and yield of the fmal immunostimulatory oligonucleotide product.

At the end of the synthesis by either linear synthesis or parallel synthesis protocols, the immunostimulatory oligonucleotides may conveniently be deprotected with concentrated ammonia solution or as recommended by the phosphoramidite supplier, if a modified nucleoside is incorporated. The product immunostimulatory oligonucleotide is preferably purfied by reversed phase HPLC, detritylated, desalted and dialyzed.

Table 4 shows representative immunostimulatory oligonucleotides according to the invention.

TABLE 4

Examples of Immunostimulatory Oligonucleotides Sequences

| COMPOUND NO. | Sequences and Modification |
|---|---|
| 1 | 5'-TCTGTR'GTTCT-X-TCTTGR'TGTCT-5' (5'-SEQ ID NO: 1-3'-X-3'-SEQ ID NO: 1-5') |

TABLE 4-continued

Examples of Immunostimulatory Oligonucleotides Sequences

| COMPOUND NO. | Sequences and Modification |
|---|---|
| 2 | 5'-ACACACCAACT-X-TCAACCACACA-5'<br>(5'-SEQ ID NO: 2-3'-X-3'-SEQ ID NO: 2-5')<br>(Control) |
| 3 | 5'-TCTGTR'GTTC$_1$U$_1$-X-U$_1$C$_1$TTGR'TGTCT-5'<br>(5'-SEQ ID NO: 3-3'-X-3'-SEQ ID NO: 3-5') |
| 4 | 5'-CTGTR'GTTCTC-X-CTCTTGR'TGTC-5'<br>(5'-SEQ ID NO: 4-3'-X-3'-SEQ ID NO: 4-5') |
| 5 | 5'-CTGTR'GTTCU$_1$C$_1$-X-C$_1$U$_1$CTTGR'TGTC-5'<br>(5'-SEQ ID NO: 5-3'-X-3'-SEQ ID NO: 5-5') |
| 6 | 5'-CTGTR'GTTC$_1$U$_1$C$_1$-X-C$_1$U$_1$C$_1$TTGR'TGTC-5'<br>(5'-SEQ ID NO: 6-3'-X-3'-SEQ ID NO: 6-5') |
| 7 | 5'-TCTGTR'GTTCT-X-CGTTCGAACGT-5'<br>(5'-SEQ ID NO: 7-3'-X-3'-SEQ ID NO: 7-5') |
| 8 | 5'-TCTGTR'GACAG-X-GACAGR'TGTCT-5'<br>(5'-SEQ ID NO: 8-3'-X-3'-SEQ ID NO: 8-5') |
| 9 | 5'-TCTGTR'GACA$_1$G$_1$-X-G$_1$A$_1$CAGR'TGTCT-5'<br>(5'-SEQ ID NO: 9-3'-X-3'-SEQ ID NO: 9-5') |
| 10 | 5'-TCAGTR'GTTAG-X-GATTGR'TGACT-5'<br>(5'-SEQ ID NO: 10-3'-X-3'-SEQ ID NO: 10-5') |
| 11 | 5'-TCAGTR'GACTG-X-GTCAGR'TGACT-5'<br>(5'-SEQ ID NO: 11-3'-X-3'-SEQ ID NO: 11-5') |
| 12 | 5'-TR'GTR'GAR'GAT-X-TAGR'AGR'TGR'T-5'<br>(5'-SEQ ID NO: 12-3'-X-3'-SEQ ID NO: 12-5') |
| 13 | 5'-TR'GTR'GTAGTA-X-ATGATGR'TGR'T-5'<br>(5'-SEQ ID NO: 13-3'-X-3'-SEQ ID NO: 13-5') |
| 14 | 5'-TR'GAAR'GTTCT-X-TCTTGR'AAGR'T-5'<br>(5'-SEQ ID NO: 14-3'-X-3'-SEQ ID NO: 14-5') |
| 15 | 5'-TR'GTAR'GTACT-X-TCATGR'ATGR'T-5' |
| 16 | 5'-TCRAACRTTCR-X-RCTTRCAARCT-5'<br>(5'-SEQ ID NO: 15-3'-X-3'-SEQ ID NO: 15-5') |

R' = 1-(2'-deoxy-β-D-ribofuranosyl)-2-oxo-7-deaza-8-methyl-purine; $A_1/C_1/G_1/U_1$ = 2'-O-methyl-ribonucleotides; R = 2'-deoxy-7-deazaguanosine; X = glycerol linker.

In a second aspect, the invention provides immunostimulatory oligonucleotide conjugates comprising an immunostimulatory oligonucleotide, as described above, and an antigen conjugated to the immunostimulatory oligonucleotide at a position other than the accessible 5' end. In some embodiments, the non-nucleotidic linker comprises an antigen, which is conjugated to the oligonucleotide. In some other embodiments, the antigen is conjugated to the oligonucleotide at a position other than its 3' end. In some embodiments, the antigen produces a vaccine effect.

The antigen is preferably selected from the group consisting of antigens associated with a pathogen, antigens associated with a cancer, antigens associated with an auto-immune disorder, and antigens associated with other diseases such as, but not limited to, veterinary or pediatric diseases. For purposes of the invention, the term "associated with" means that the antigen is present when the pathogen, cancer, auto-immune disorder, food allergy, respiratory allergy, asthma or other disease is present, but either is not present, or is present in reduced amounts, when the pathogen, cancer, auto-immune disorder, food allergy, respiratory allergy, or disease is absent.

The immunostimulatory oligonucleotide is covalently linked to the antigen, or it is otherwise operatively associated with the antigen. As used herein, the term "operatively associated with" refers to any association that maintains the activity of both immunostimulatory oligonucleotide and antigen. Nonlimiting examples of such operative associations include being part of the same liposome or other such delivery vehicle or reagent. In embodiments wherein the immunostimulatory oligonucleotide is covalently linked to the antigen, such covalent linkage preferably is at any position on the immunostimulatory oligonucleotide other than an accessible 5' end of an immunostimulatory oligonucleotide. For example, the antigen may be attached at an internucleoside linkage or may be attached to the non-nucleotidic linker. Alternatively, the antigen may itself be the non-nucleotidic linker.

In a third aspect, the invention provides pharmaceutical formulations comprising an immunostimulatory oligonucleotide or immunostimulatory oligonucleotide conjugate according to the invention and a physiologically acceptable carrier. As used herein, the term "physiologically acceptable" refers to a material that does not interfere with the effectiveness of the immunostimulatory oligonucleotide and is compatible with a biological system such as a cell, cell culture, tissue, or organism. Preferably, the biological system is a living organism, such as a vertebrate.

As used herein, the term "carrier" encompasses any excipient, diluent, filler, salt, buffer, stabilizer, solubilizer, lipid, or other material well known in the art for use in pharmaceutical formulations. It will be understood that the characteristics of the carrier, excipient, or diluent will depend on the route of administration for a particular application. The preparation of pharmaceutically acceptable formulations containing these materials is described in, e.g., *Remington's Pharmaceutical Sciences,* 18th Edition, ed. A. Gennaro, Mack Publishing Co., Easton, Pa., 1990.

In a fourth aspect, the invention provides methods for generating an immune response in a vertebrate, such methods comprising administering to the vertebrate an immunostimulatory oligonucleotide or immunostimulatory oligonucleotide conjugate according to the invention. In some embodiments, the vertebrate is a mammal. For purposes of this invention, the term "mammal" is expressly intended to include humans. In preferred embodiments, the immunostimulatory oligonucleotide or immunostimulatory oligonucleotide conjugate is administered to a vertebrate in need of immunostimulation.

In the methods according to this aspect of the invention, administration of immunostimulatory oligonucleotide or immunostimulatory oligonucleotide conjugate can be by any suitable route, including, without limitation, parenteral, oral, sublingual, transdermal, topical, intranasal, aerosol, intraocular, intratracheal, intrarectal, vaginal, by gene gun, dermal patch or in eye drop or mouthwash form. Administration of the therapeutic compositions of immunostimulatory oligonucleotides can be carried out using known procedures at dosages and for periods of time effective to reduce symptoms or surrogate markers of the disease. When administered systemically, the therapeutic composition is preferably administered at a sufficient dosage to attain a blood level of immunostimulatory oligonucleotide from about 0.0001 micromolar to about 10 micromolar. For localized administration, much lower concentrations than this may be effective, and much higher concentrations may be tolerated. Preferably, a total dosage of immunostimulatory oligonucleotide ranges from about 0.001 mg per patient per day to about 200 mg per kg body weight per day. It may be desirable to administer simultaneously, or sequentially a therapeutically effective amount of one or more of the therapeutic compositions of the invention to an individual as a single treatment episode.

In certain preferred embodiments, immunostimulatory oligonucleotide or immunostimulatory oligonucleotide conjugate according to the invention are administered in combination with vaccines, antibodies, cytotoxic agents, allergens, antibiotics, antisense oligonucleotides, peptides, proteins, gene therapy vectors, DNA vaccines and/or adjuvants to enhance the specificity or magnitude of the immune response. In these embodiments, the immunostimulatory oligonucleotides of the invention can variously act as adjuvants and/or produce direct immunostimulatory effects.

Either the immunostimulatory oligonucleotide or immunostimulatory oligonucleotide conjugate or the vaccine, or both, may optionally be linked to an immunogenic protein, such as keyhole limpet hemocyanin (KLH), cholera toxin B subunit, or any other immunogenic carrier protein. Any of the plethora of adjuvants may be used including, without limitation, Freund's complete adjuvant, KLH, monophosphoryl lipid A (MPL), alum, and saponins, including QS-21, imiquimod, R848, or combinations thereof.

For purposes of this aspect of the invention, the term "in combination with" means in the course of treating the same disease in the same patient, and includes administering the immunostimulatory oligonucleotide and/or the vaccine and/or the adjuvant in any order, including simultaneous administration, as well as temporally spaced order of up to several days apart. Such combination treatment may also include more than a single administration of the immunostimulatory oligonucleotide, and/or independently the vaccine, and/or independently the adjuvant. The administration of the immunostimulatory oligonucleotide and/or vaccine and/or adjuvant may be by the same or different routes.

The methods according to this aspect of the invention are useful for model studies of the immune system. The methods are also useful for the prophylactic or therapeutic treatment of human or animal disease. For example, the methods are useful for pediatric and veterinary vaccine applications.

In a fifth aspect, the invention provides methods for therapeutically treating a patient having a disease or disorder, such methods comprising administering to the patient an immunostimulatory oligonucleotide or immunostimulatory oligonucleotide conjugate according to the invention. In various embodiments, the disease or disorder to be treated is cancer, an autoimmune disorder, airway inflammation, inflammatory disorders, allergy, asthma or a disease caused by a pathogen. Pathogens include bacteria, parasites, fungi, viruses, viroids and prions. Administration is carried out as described for the fourth aspect of the invention.

For purposes of the invention, the term "allergy" includes, without limitation, food allergies and respiratory allergies. The term "airway inflammation" includes, without limitation, asthma. As used herein, the term "autoimmune disorder" refers to disorders in which "self" proteins undergo attack by the immune system. Such term includes autoimmune asthma.

In any of the methods according to this aspect of the invention, the immunostimulatory oligonucleotide or immunostimulatory oligonucleotide conjugate can be administered in combination with any other agent useful for treating the disease or condition that does not diminish the immunostimulatory effect of the immunostimulatory oligonucleotide. For example, in the treatment of cancer, it is contemplated that the immunostimulatory oligonucleotide or immunostimulatory oligonucleotide conjugate may be administered in combination with a chemotherapeutic compound.

The examples below are intended to further illustrate certain preferred embodiments of the invention, and are not intended to limit the scope of the invention.

EXAMPLES

Example 1

Synthesis of Oligonucleotides Containing Immunostimulatory Moieties

Oligonucleotides were synthesized on a 1 µmol to 0.1 mM scale using an automated DNA synthesizer (OligoPilot II, AKTA, (Amersham) and/or Expedite 8909 (Applied Biosystem)), following the linear synthesis or parallel synthesis procedures outlined in FIGS. 3 and 4.

5'-DMT dA, dG, dC and T phosphoramidites were purchased from Proligo (Boulder, Colo.). 5'-DMT 7-deaza-dG and araG phosphoramidites were obtained from Chemgenes (Wilmington, Mass.). DiDMT-glycerol linker solid support was obtained from Chemgenes. 1-(2'-deoxy-β-D-ribofuranosyl)-2-oxo-7-deaza-8-methyl-purine amidite was obtained from Glen Research (Sterling, Va.), 2'-O-methylribonuncleoside amidites were obtained from Promega (Obispo, Calif.). All oligonucleotides were phosphorothioate backbone modified.

All nucleoside phosphoramidites were characterized by $^{31}$P and $^{1}$H NMR spectra. Modified nucleosides were incorporated at specific sites using normal coupling cycles recommended by the supplier. After synthesis, oligonucleotides were deprotected using concentrated ammonium hydroxide and purified by reverse phase HPLC, detritylation, followed by dialysis. Purified oligonucleotides as sodium salt form were lyophilized prior to use. Purity was tested by CGE and MALDI-TOF MS. Endotoxin levels were determined by LAL test and were below 1.0 EU/mg.

Example 2

Figure 6:
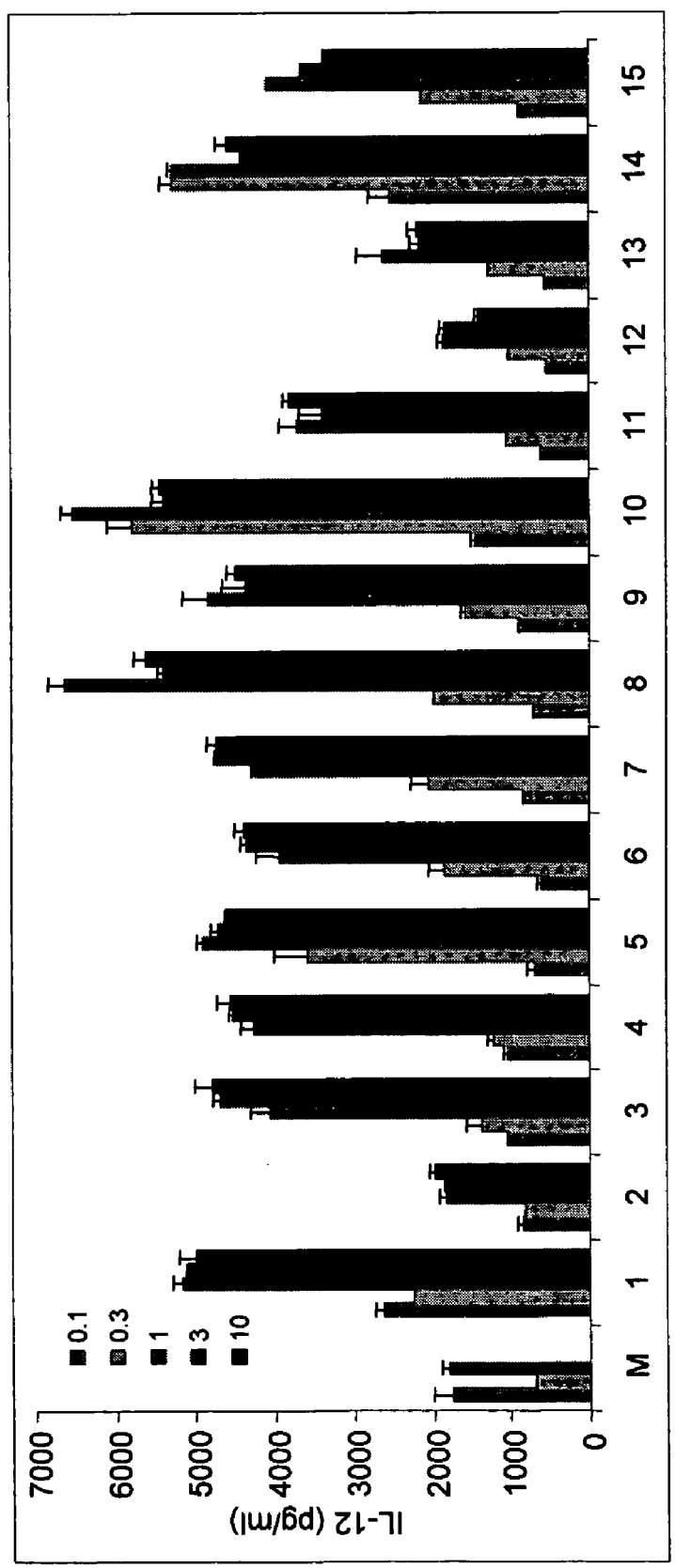
FIG. 6 shows IL-12 induction in C57BL/6 mouse spleen cell cultures by immunostimulatory oligonucleotide compounds 1-15 as depicted in Table 4.
Figure 7:
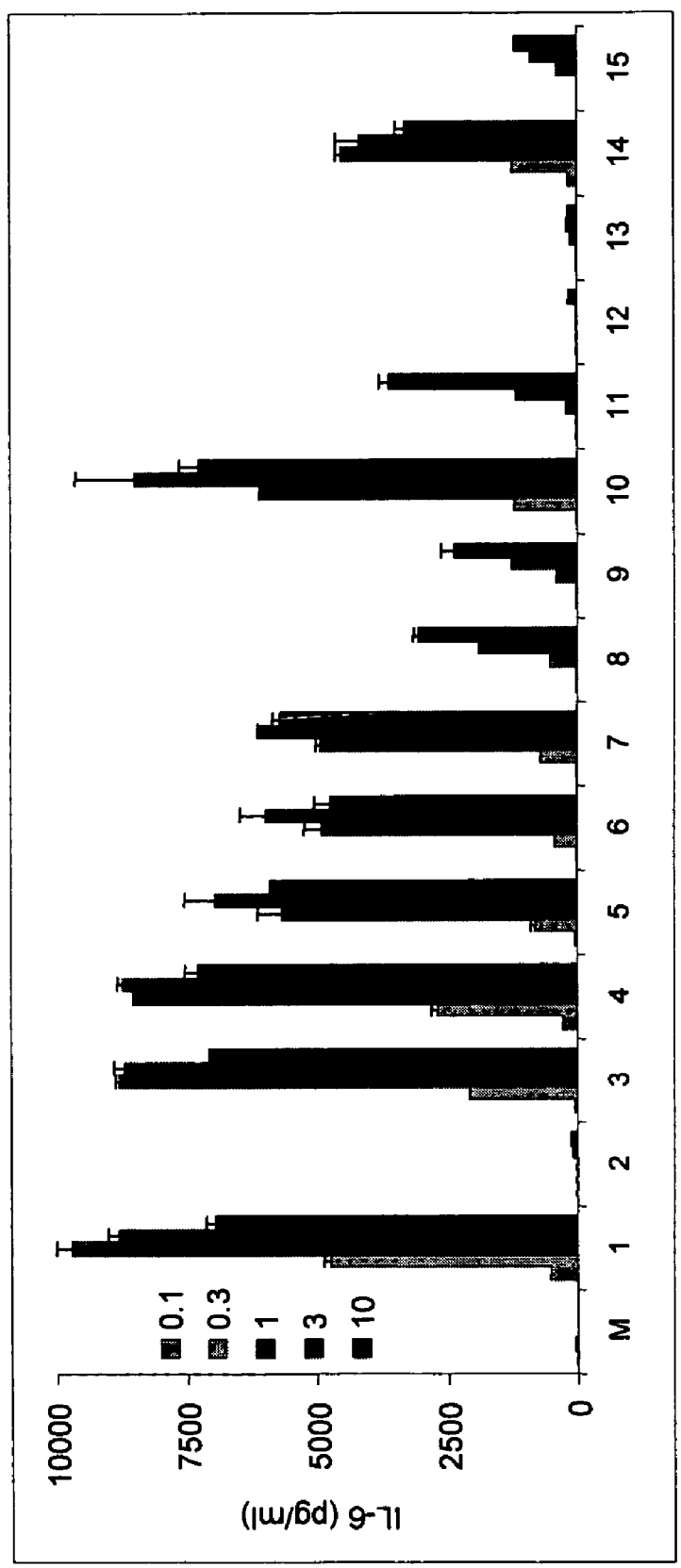
FIG. 7 shows IL-6 induction in C57BL/6 mouse spleen cell cultures by immunostimulatory oligonucleotide compounds 1-15 as depicted in Table 4.
Figure 8:
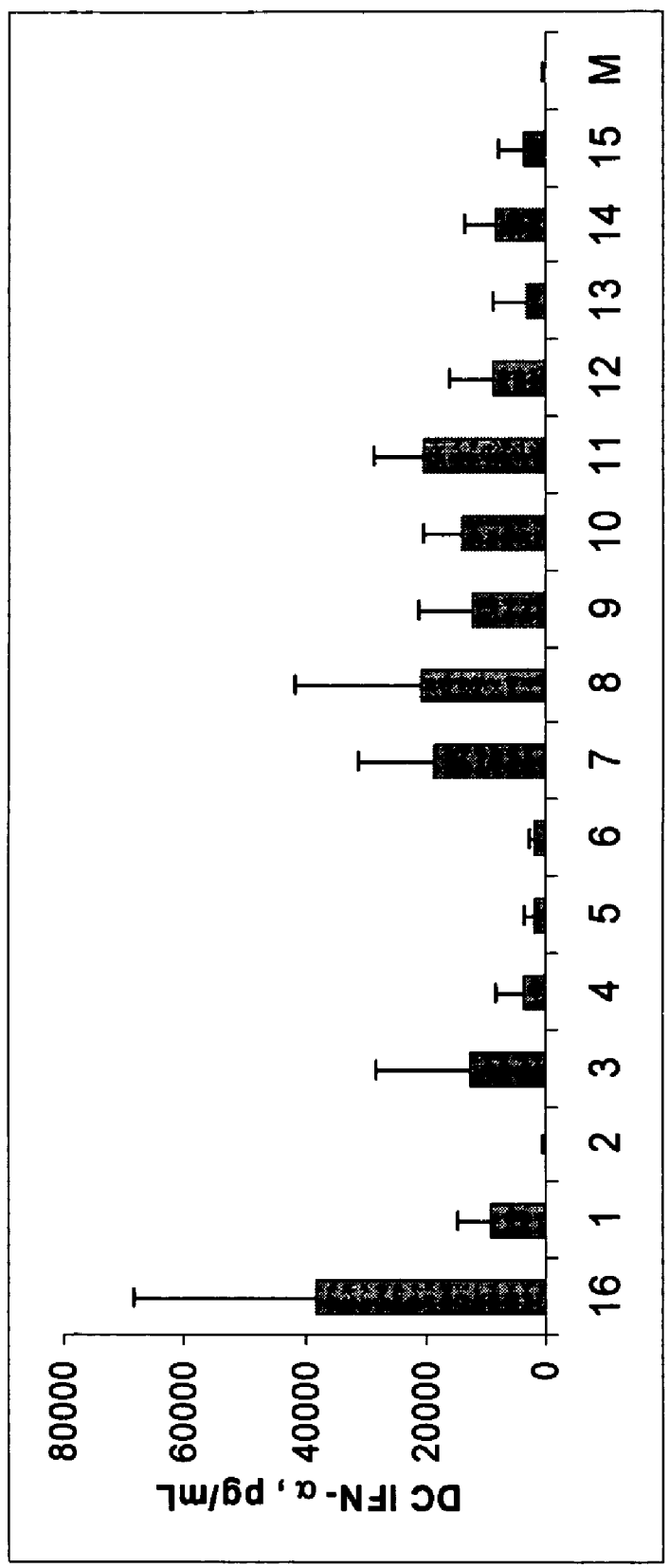
FIG. 8 shows IFN-α induction in human pDC cultures by immunostimulatory oligonucleotide compounds 1-16 as depicted in Table 4.
Figure 9:
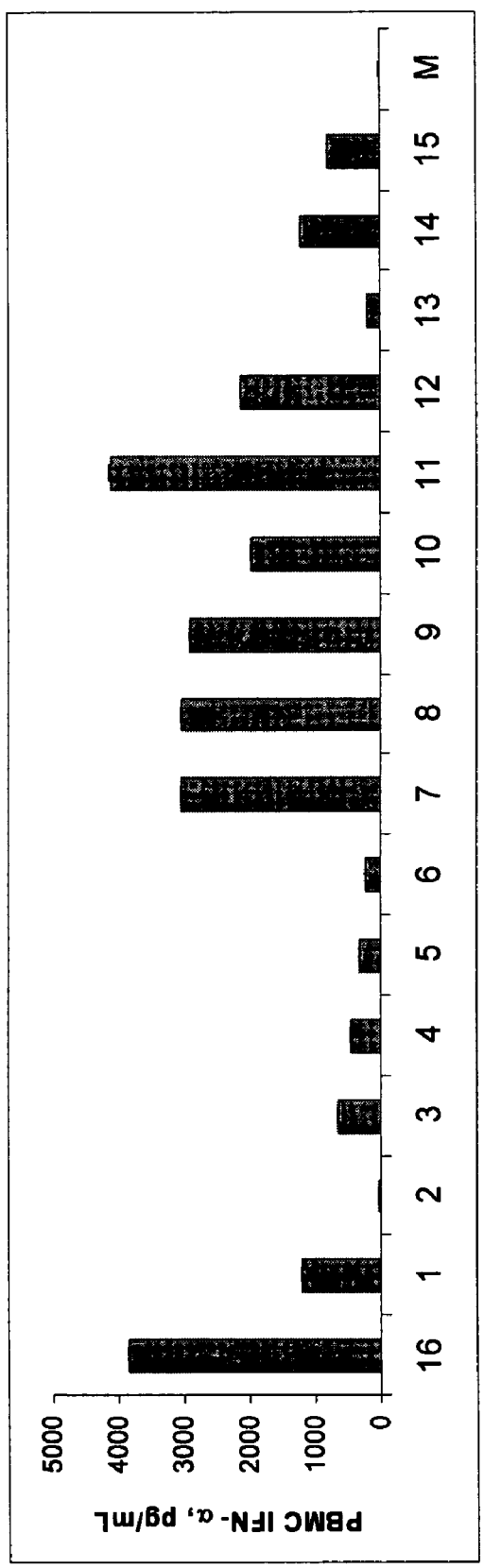
FIG. 9 shows IFN-α induction in human PBMC cultures by immunostimulatory oligonucleotide compounds 1-16 as depicted in Table 4.
Figure 10:
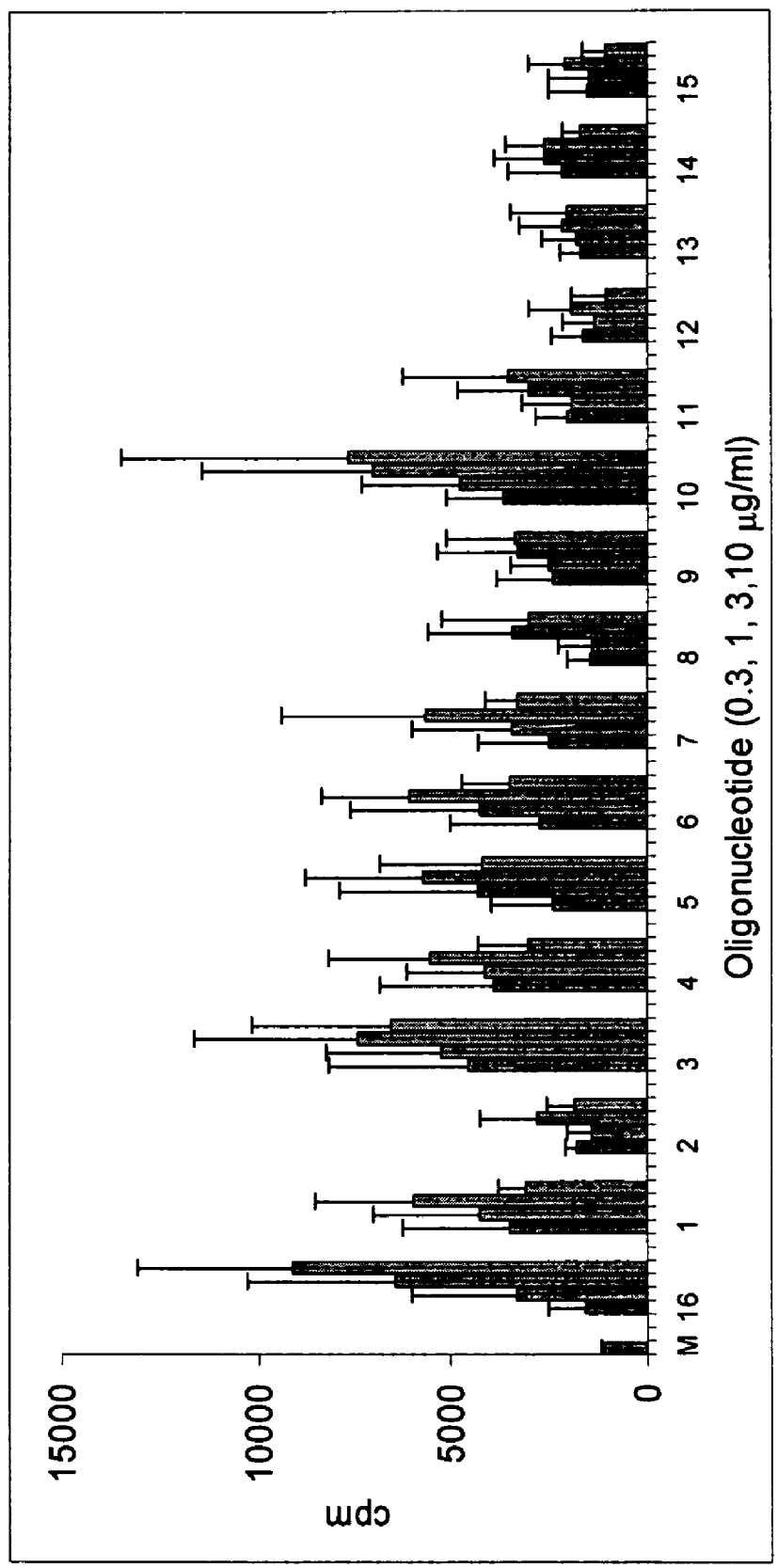
FIG. 10 shows Human B cell proliferation by immunostimulatory oligonucleotide compounds 1-16 as depicted in Table 4.

Activity of Short-immunostimulatory Oligonucleotides in Murine Spleen Cell Cultures C57/BL6 spleen cells were cultured with indicated concentrations of compounds. After 24 hours the supernatants were collected and the levels of IL-12 and IL-6 were determined by ELISA. All immunostimulatory oligonucleotides showed a concentration-dependent induction of two typical cytokines, IL-12 and IL-6 (FIGS. 6-7).

Example 3

Need Protocol for IFN-alpha Induction in Human pDC

Peripheral blood mononuclear cells (PBMCs) from freshly drawn healthy volunteer blood (CBR Laboratories, Boston, Mass.) were isolated by Ficoll density gradient centrifugation

Example 4

IFN-alpha Induction in Human PMBC

Human PBMCs were plated in 48-well plates using 5×10⁶ cells/ml. The IMOs dissolved in DPBS (pH 7.4; Mediatech) were added to a final concentration of 10.0 μg/ml to the cell cultures. The cells were then incubated at 37° C. for 24 hr and the supernatants were collected for ELISA assays. The experiments were performed in triplicate wells. The levels of IFN-α were measured by sandwich ELISA. The required reagents, including cytokine antibodies and standards, were purchased from PharMingen.

method (Histopaque-1077, Sigma). pDCs were isolated from PBMCs by positive selection using the BDCA4 cell isolation kits (Miltenyi Biotec) according to the manufacturer's instructions. pDCs were plated in 96-well dishes using 1×10⁶ cells/ml. The IMOs dissolved in DPBS (pH 7.4; Mediatech) were added to a final concentration of 10.0 μg/ml to the cell cultures. The cells were then incubated at 37° C. for 24 hr and the supernatants were collected for ELISA assays. The experiments were performed in triplicate wells. The levels of IFN-α were measured by sandwich ELISA. The required reagents, including cytokine antibodies and standards, were purchased from PharMingen.

Example 5

Human B-cell Proliferation

The culture medium used for the assay consisted of RPMI 1640 medium supplemented with 1.5 mM glutamine, 1 mM sodium pyruvate, 0.1 mM non-essential amino acids, 50 μM 2-mercaptoethanol, 100 IU/ml penicillin-streptomycin mix and 10% heat-inactivated fetal bovine serum. A total of 0.5× 10⁶ B cells per ml (i.e. 1×10⁵/200 μl/well) were stimulated in 96 well flat bottom plates with different concentrations of test oligonucleotides in triplicate for a total period of 72 hours. After 66 h, cells were pulsed with 0.75 μCi of [³H]-thymidine (1 Ci=37 GBq; Perkin Elmer Life Sciences) in 20 μl RPMI 1640 medium (no serum) per well and harvested 8 h later. The plates were then harvested using a cell harvester and radio-active incorporation was determined using standard liquid scintillation technique. The results are expressed either as mean cpm+/−SD or as proliferation index (cpm treated group/cpm medium control).

EQUIVALENTS

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. An immunostimulatory oligonucleotide having a structure from the group of
   5'-TCTGTR'GTTC$_1$U$_1$-X-U$_1$C$_1$TTGR'TGTCT-5'
      (5'-SEQ ID NO: 3-3'-X-3'-SEQ ID NO: 3-5');
   5'-CTGTR'GTTCU$_1$C$_1$-X-C$_1$U$_1$CTTGR'TGTC-5'
      (5'-SEQ ID NO: 5-3'-X-3'-SEQ ID NO: 5-5');
   5'-CTGTR'GTTC$_1$U$_1$C$_1$-X-C$_1$U$_1$C$_1$TTGR'TGTC-5'
      (5'-SEQ ID NO: 6-3'-X-3'-SEQ ID NO: 6-5');
   5'-TCTGTR'GTTCT-X-CGTTCGAACGT-5' (5'-SEQ ID NO: 7-3'-X-3'-SEQ ID NO: 17-5');
   5'-TCTGTR'GACAG-X-GACAGR'TGTCT-5' (5'-SEQ ID NO: 8-3'-X-3'-SEQ ID NO: 8-5');
   5'-TCTGTR'GACA$_1$G$_1$-X-G$_1$A$_1$CAGR'TGTCT-5'
      (5'-SEQ ID NO: 9-3'-X-3'-SEQ ID NO: 9-5');
   5'-TCAGTR'GTTAG-X-GATTGR'TGACT-5' (5'-SEQ ID NO: 10-3'-X-3'-SEQ ID NO: 10-5');
   5'-TCAGTR'GACTG-X-GTCAGR'TGACT-5' (5'-SEQ ID NO: 11-3'-X-3'-SEQ ID NO: 11-5');
   5'-TR'GTR'GAR'GAT-X-TAGR'AGR'TGR'T-5'(5'-SEQ ID NO: 12-3'-X-3'-SEQ ID NO: 12-5');
   5'-TR'GTR'GTAGTA-X-ATGATGR'TGR'T-5' (5'-SEQ ID NO: 13-3'-X-3'-SEQ ID NO: 13-5');
   5'-TR'GAAR'GTTCT-X-TCTTGR'AAGR'T-5' (5'-SEQ ID NO: 14-3'-X-3'-SEQ ID NO: 14-5'); and
   5'-TR'GTAR'GTACT-X-TCATGR'ATGR'T-5' (5'-SEQ ID NO: 15-3'-X-3'-SEQ ID NO: 15-5'), wherein R'=1-(2'-deoxy-β-D-ribofuranosyl)-2-oxo-7-deaza-8-methyl-purine; A$_1$/C$_1$/G$_1$/U$_1$=2'-O-methyl-ribonucleotides; R=2'-deoxy-7-deazaguanosine and X=glycerol linker.

2. An immunostimulatory oligonucleotide according to claim 1 having the structure 5'-TCTGTR'GTTC$_1$U$_1$-X-U$_1$C$_1$TTGR'TGTCT-5' (5'-SEQ ID NO: 3-3'-X-3'-SEQ ID NO: 3-5').

3. An immunostimulatory oligonucleotide according to claim 1 having the structure 5'-CTGTR'GTTCU$_1$C$_1$-X-C$_1$U$_1$CTTGR'TGTC-5' (5'-SEQ ID NO: 5-3'-X-3'-SEQ ID NO: 5-5').

4. An immunostimulatory oligonucleotide according to claim 1 having the structure 5'-CTGTR'GTTC$_1$U$_1$C$_1$-X-C$_1$U$_1$C$_1$TTGR'TGTC-5' (5'-SEQ ID NO: 6-3'-X-3'-SEQ ID NO: 6-5').

5. An immunostimulatory oligonucleotide according to claim 1 having the structure 5'-TCTGTR'GTTCT-X-CGTTCGAACGT-5' (5'-SEQ ID NO: 7-3'-X-3'-SEQ ID NO: 17-5').

6. An immunostimulatory oligonucleotide according to claim 1 having the structure 5'-TCTGTR'GACAG-X-GACAGR'TGTCT-5' (5'-SEQ ID NO: 8-3'-X-3'-SEQ ID NO: 8-5').

7. An immunostimulatory oligonucleotide according to claim 1 having the structure 5'-TCTGTR'GACA$_1$U$_1$-X-G$_1$A$_1$CAGR'TGTCT-5' (5'-SEQ ID NO: 9-3'-X-3'-SEQ ID NO: 9-5').

8. An inimunostimulatory oligonucleotide according to claim 1 having the structure 5'-TCAGTR'GTTAG-X-GATTGR'TGACT-5' (5'-SEQ ID NO: 10-3'-X-3'-SEQ ID NO: 10-5').

9. An immunostimulatory oligonucleotide according to claim 1 having the structure 5'-TCAGTR'GACTG-X-GTCAGR'TGACT-5' (5'-SEQ ID NO: 11-3'-X-3'-SEQ ID NO: 11-5').

10. An immunostimulatory oligonucleotide according to claim 1 having the structure 5'-TR'GTR'GAR'GAT-X-TAGR'AGR'TGR'T-5' (5'-SEQ ID NO: 12-3'-X-3'-SEQ ID NO: 12-5').

11. An immunostimulatory oligonucleotide according to claim 1 having the structure 5'-TR'GTR'GTAGTA-X-ATGATGR'TGR'T-5' (5'-SEQ ID NO: 13-3'-X-3'-SEQ ID NO: 13-5').

12. An immunostimulatory oligonucleotide according to claim 1 having the structure 5'-TR'GAAR'GTTCT-X-TCTTGR'AAGR'T-5' (5'-SEQ ID NO: 14-3'-X-3'-SEQ ID NO: 14-5').

13. An immunostimulatory oligonucleotide according to claim 1 having the structure 5'-TR'GTAR'GTACT-X-TCATGR'ATGR'T-5' (5'-SEQ ID NO: 15-3'-X-3'-SEQ ID NO: 15-5').

14. A pharmaceutical formulation comprising the oligonucleotide according to claim 1 and a physiologically acceptable carrier.

15. A method for generating an inmune response in a vertebrate, the method comprising administering to the vertebrate an immunostimulatory oligonucleotide having a structure from the group of 5'-TCTGTR'GTTC$_1$U$_1$-X-U$_1$C$_1$TTGR'TGTCT-5' (5'-SEQ ID NO: 3-3'-X-3'-SEQ ID NO: 3-5');
   5'-CTGTR'GTTCU$_1$C$_1$-X-C$_1$U$_1$CTTGR'TGTC-5'
      (5'-SEQ ID NO: 5-3'-X-3'-SEQ ID NO: 5-5');
   5'-CTGTR'GTTC$_1$U$_1$C$_1$-X-C$_1$U$_1$C$_1$TTGR'TGTC-5'
      (5'-SEQ ID NO: 6-3'-X-3'-SEQ ID NO: 6-5');
   5'-TCTGTR'GTTCT-X-CGTTCGAACGT-5' (5'-SEQ ID NO: 7-3'-X-3'-SEQ ID NO: 17-5');
   5'-TCTGTR'GACAG-X-GACAGR'TGTCT-5' (5'-SEQ ID NO: 8-3'-X-3'-SEQ ID NO: 8-5');
   5'-TCTGTR'GACA$_1$G$_1$-X-G$_1$A$_1$CAGR'TGTCT-5'
      (5'-SEQ ID NO: 9-3'-X-3'-SEQ ID NO: 9-5');
   5'-TCAGTR'GTTAG-X-GATTGR'TGACT-5' (5'-SEQ ID NO: 10-3'-X-3'-SEQ ID NO: 10-5');
   5'-TCAGTR'GACTG-X-GTCAGR'TGACT-5' (5'-SEQ ID NO: 11-3'-X-3'-SEQ ID NO: 11-5');
   5'-TR'GTR'GAR'GAT-X-TAGR'AGR'TGR'T-5' (5'-SEQ ID NO: 12-3'-X-3'-SEQ ID NO: 12-5');
   5'-TR'GTR'GTAGTA-X-ATGATGR'TGR'T-5' (5'-SEQ ID NO: 13-3'-X-3'-SEQ ID NO: 13-5');
   5'-TR'GAAR'GTTCT-X-TCTTGR'AAGR'T-5' (5'-SEQ ID NO: 14-3'-X-3'-SEQ ID NO: 14-5'); and
   5'-TR'GTAR'GTACT-X-TCATGR'ATGR'T-5' (5'-SEQ ID NO: 15-3'-X-3'-SEQ ID NO: 15-5'), wherein R'=1-(2'-deoxy-β-D-ribofuranosyl)-2-oxo-7-deaza-8-methyl-purine; A$_1$/C$_1$/G$_1$/U$_1$=2'-O-methyl-ribonucleotides; R=2'-deoxy-7-deazaguanosine and X=glycerol linker.

16. The method according to claim 15, wherein the route of administration is selected from parenteral, oral, sublingual, transdermal, topical, intranasal, aerosol, intraocular, intratracheal, intrarectal, vaginal, gene gun, dermal patch, eye drop and mouthwash.

17. The method according to claim 15 comprising administering an immunostimulatory oligonucleotide having the structure 5'-TCTGTR'GTTC$_1$U$_1$-X-U$_1$C$_1$TTGR'TGTCT-5' (5'-SEQ ID NO: 3-3'-X-3'-SEQ ID NO: 3-5').

18. The method according to claim 15 comprising administering an immunostimulatory oligonucleotide having the structure 5'-CTGTR'GTTCU$_1$C$_1$-X-C$_1$U$_1$CTTGR'TGTC-5' (5'-SEQ ID NO: 5-3'-X-3'-SEQ ID NO: 5-5').

19. The method according to claim 15 comprising administering an immunostimulatory oligonucleotide having the structure 5'-CTGTR'GTTC$_1$U$_1$C$_1$-X-C$_1$U$_1$C$_1$TTGR'TGTC-5' (5'-SEQ ID NO: 6-3'-X-3'-SEQ ID NO: 6-5').

20. The method according to claim 15 comprising administering an inimunostimulatory oligonucleotide having the structure 5'-TCTGTR'GTTCT-X-GTTCGAACGT-5' (5'-SEQ ID NO: 7-3'-X-3'-SEQ ID NO: 17-5').

21. The method according to claim 15 comprising administering an immunostimulatory oligonucleotide having the structure 5'-TCTGTR'GACAG-X-GACAGR'TGTCT-5' (5'-SEQ ID NO: 8-3'-X-3'-SEQ ID NO: 8-5').

22. The method according to claim 15 comprising administering an immunostimulatory oligonucleotide having the structure 5'-TCTGTR'GACA$_1$G$_1$-X-G$_1$A$_1$CAGR'TGTCT-5' (5'-SEQ ID NO: 9-3'-X-3'-SEQ ID NO: 9-5').

23. The method according to claim 15 comprising administering an immunostimulatory oligonucleotide having the structure 5'-TCAGTR'GTTAG-X-GATTGR'TGACT-5' (5'-SEQ ID NO: 10-3'-X-3'-SEQ ID NO: 10-5').

24. The method according to claim 15 comprising administering an immunostimulatory oligonucleotide having the structure 5'-TCAGTR'GACTG-X-GTCAGR'TGACT-5' (5'-SEQ ID NO: 11-3'-X-3'-SEQ ID NO: 11-5').

25. The method according to claim 15 comprising administering an immunostimulatory oligonucleotide having the structure 5'-TR'GTR'GAR'GAT-X-TAGR'AGR'TGR'T-5' (5'-SEQ ID NO: 12-3'-X-3'-SEQ ID NO: 12-5').

26. The method according to claim 15 comprising administering an immunostimulatory oligonucleotide having the structure 5'-TR'GTR'GTAGTA-X-ATGATGR'TGR'T-5'(5'-SEQ ID NO: 13-3'-X-3'-SEQ ID NO: 13-5').

27. The method according to claim 15 comprising administering an immunostimulatory oligonucleotide having the structure 5'-TR'GAAR'GTTCT-X-TCTTGR'AAGR'T-5' (5'-SEQ ID NO: 14-3'-X-3'-SEQ ID NO: 14-5').

28. The method according to claim 15 comprising administering an immunostimulatory oligonucleotide having the structure 5'-TR'GTAR'GTACT-X-TCATGR'ATGR'T-5' (5'-SEQ ID NO: 15-3'-X-3'-SEQ ID NO: 15-5').

29. The oligonucleotide according to claim 1, further comprising an antibody, antisense oligonucleotide, protein, antigen, allergen, chemotherapeutic agent or adjuvant.

30. The pharmaceutical composition according to claim 14, further comprising an antibody, antisense oligonucleotide, protein, antigen, allergen, chemotherapeutic agent or adjuvant.

31. The method according to claim 15, further comprising administering an antibody, antisense oligonucleotide, protein, antigen, allergen, chemotherapeutic agent or adjuvant.

* * * * *